United States Patent [19]
Carriazo et al.

[11] Patent Number: 5,980,543
[45] Date of Patent: Nov. 9, 1999

[54] MICROKERATOME AND METHOD OF PERFORMING CORNEAL RESECTIONS

[75] Inventors: César C. Carriazo, Barranquilla; Jose I. Barraquer; Jose I. Barraquer, Jr., both of Bogota, all of Colombia

[73] Assignee: Instituto Barraquer de America, Bogota, Colombia

[21] Appl. No.: 09/002,515

[22] Filed: Jan. 2, 1998

Related U.S. Application Data

[63] Continuation-in-part of application No. 08/772,698, Dec. 23, 1996, abandoned
[60] Provisional application No. 60/056,775, Aug. 25, 1997.

[51] Int. Cl.$^6$ .................................................. A61B 17/32
[52] U.S. Cl. .................................... 606/166; 606/180
[58] Field of Search ................................ 606/166, 180, 606/167

[56] References Cited

U.S. PATENT DOCUMENTS

| | | | |
|---|---|---|---|
| Re. 35,421 | 1/1997 | Ruiz et al. | 606/166 |
| 4,173,980 | 11/1979 | Curtin | 128/303 R |
| 4,660,556 | 4/1987 | Swinger et al. | 128/305 |
| 4,662,370 | 5/1987 | Hoffman et al. | 128/305 |
| 4,665,914 | 5/1987 | Tanne | 128/305 |
| 4,674,503 | 6/1987 | Peyman et al. | 128/305 |
| 4,688,570 | 8/1987 | Kramer et al. | 128/305 |
| 4,840,175 | 6/1989 | Peyman | 128/303.1 |
| 5,133,726 | 7/1992 | Ruiz et al. | 606/166 |
| 5,318,046 | 6/1994 | Rozakis | 606/166 X |
| 5,342,378 | 8/1994 | Giraud et al. | 606/166 |
| 5,496,339 | 3/1996 | Koepnick | 606/166 |
| 5,586,980 | 12/1996 | Kremer et al. | 606/4 |
| 5,591,174 | 1/1997 | Clark et al. | 606/166 X |
| 5,591,195 | 1/1997 | Kilmer et al. | 606/166 |
| 5,595,570 | 1/1997 | Smith | 606/166 |
| 5,624,456 | 4/1997 | Hellenkamp | 606/166 |

FOREIGN PATENT DOCUMENTS

| | | | |
|---|---|---|---|
| 0771553A1 | 5/1997 | European Pat. Off. | A61F 9/00 |

OTHER PUBLICATIONS

Advanced Microkeratome Simplifies ALK, by Bob Kronemyer, Dec. 15, 1995.
The Lasik Experience, Excimer Laser ALK (ALK–E) ©1996 Maddoz Excimer Laser Center.
Surgeons Believe LASIK Superior to ALK, by Deborah Catalano Ruiani, Jan. 1, 1996.
Keratomileusis, reprinted from International Surgery, vol. 48, No. 2, Aug., 1967, by Jose I. Barraquer, M.D., Bogota, Colombia.

*Primary Examiner*—Michael H. Thaler
*Attorney, Agent, or Firm*—Felsman, Bradley, Vaden, Gunter & Dillon, LLP

[57] ABSTRACT

A microkeratome and related surgical methods for performing lamellar keratotomies are provided. The microkeratome includes a guide ring assembly for placement on the eyeball, or ocular globe such that the globe's cornea protrudes therethrough. The guide ring can be temporarily fixed to the ocular globe, immobilizing the eyeball relative to the instrument. A cutting blade suitable for corneal resections is carried in a cutting head over the guide ring through a cutting path defined by the guide ring. An adjustable float head, also generally known as a plaque, is connected to the cutting head for at least partially compressing the cornea ahead of the blade, so as to set the desired thickness of the corneal resection. The cutting head and float head can be driven across the guide ring, whereby the blade cuts at least partially through the cornea to perform the lamellar keratotomy. Various surgical corrections are obtainable through the use of arcuate and oblique plaques, as an alternative to planar plaques or float heads, where appropriate.

20 Claims, 22 Drawing Sheets

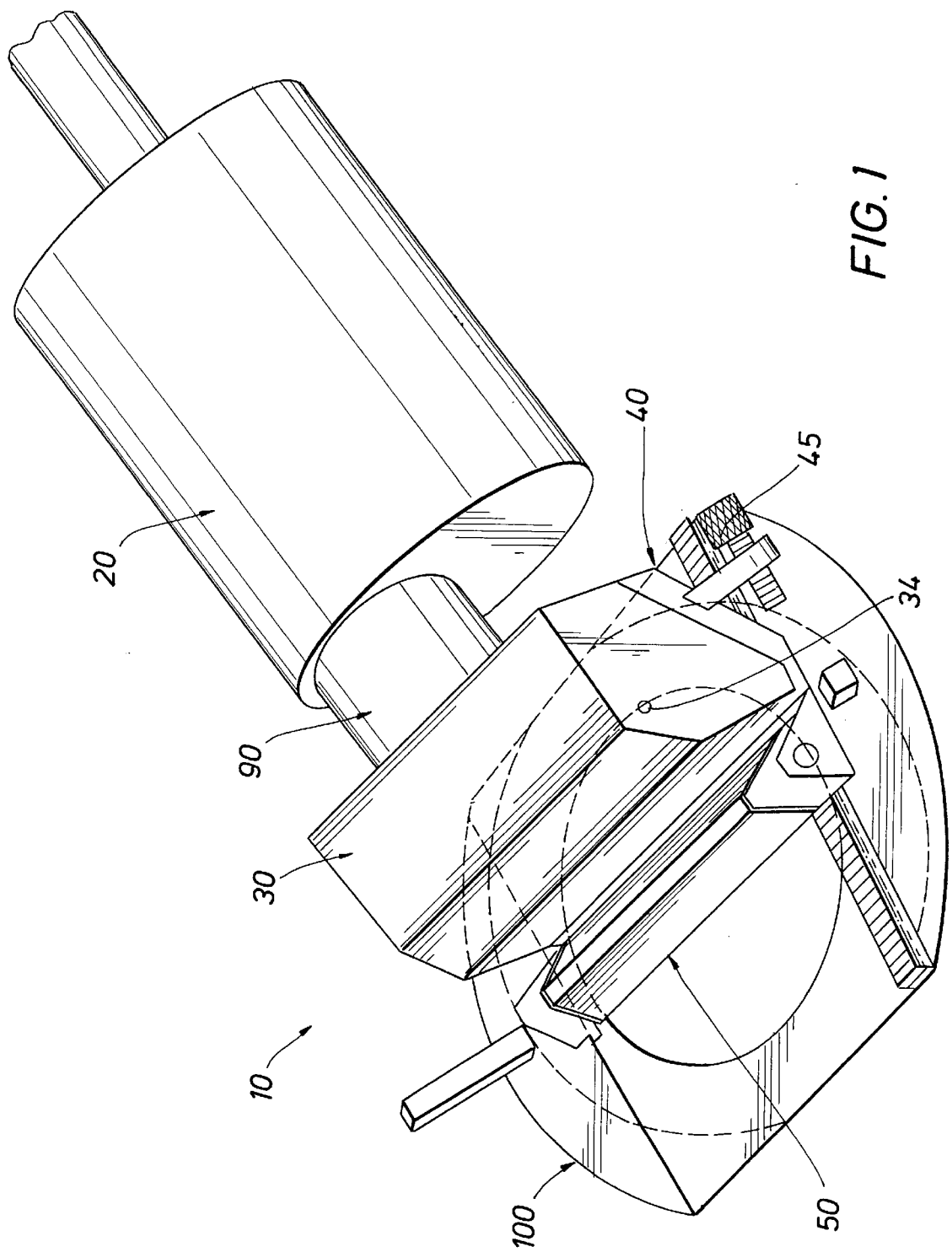

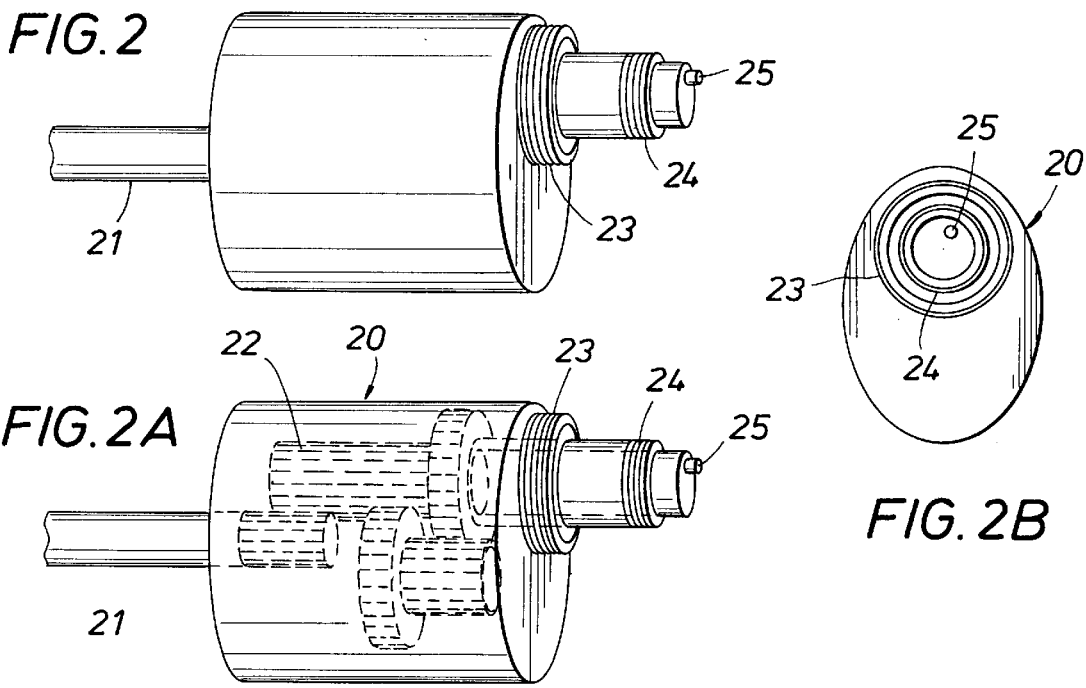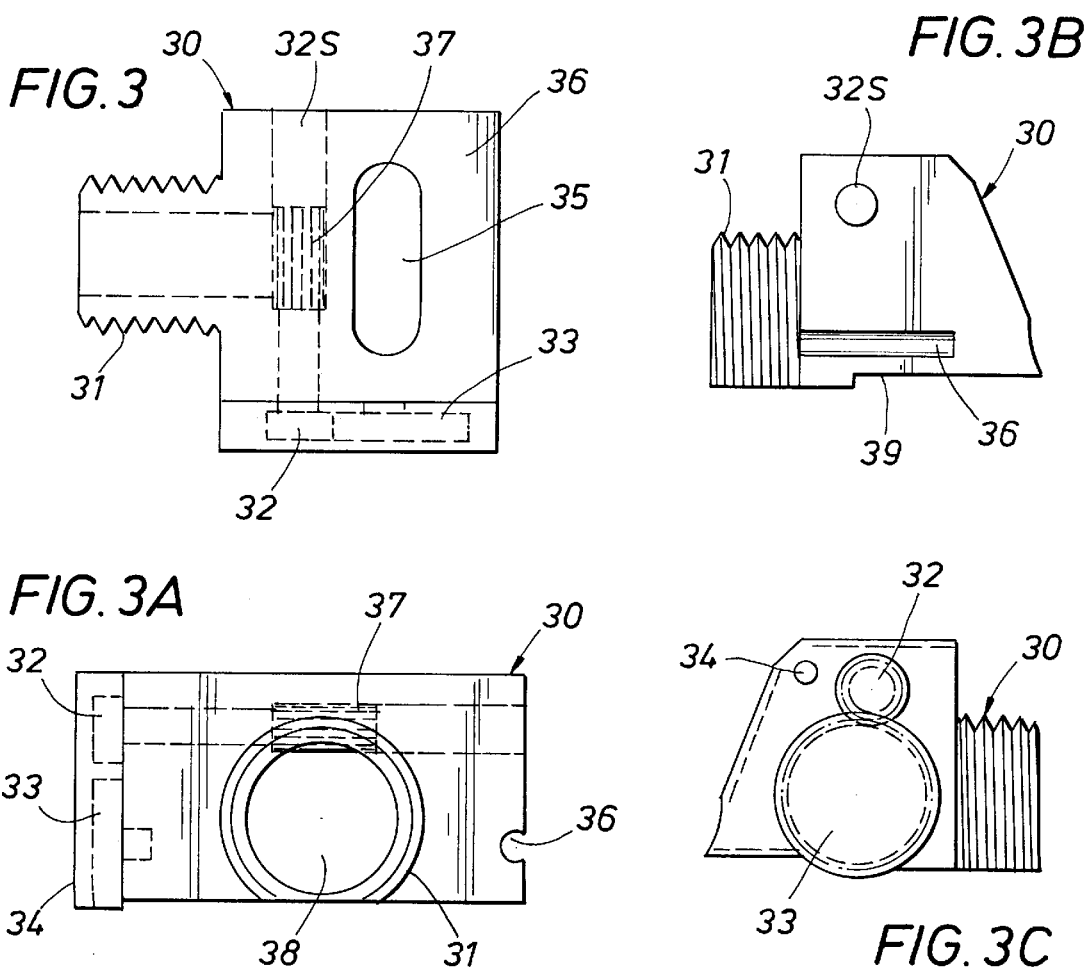

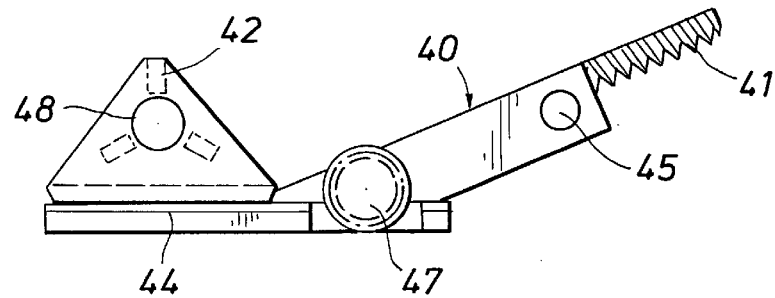
FIG. 4A
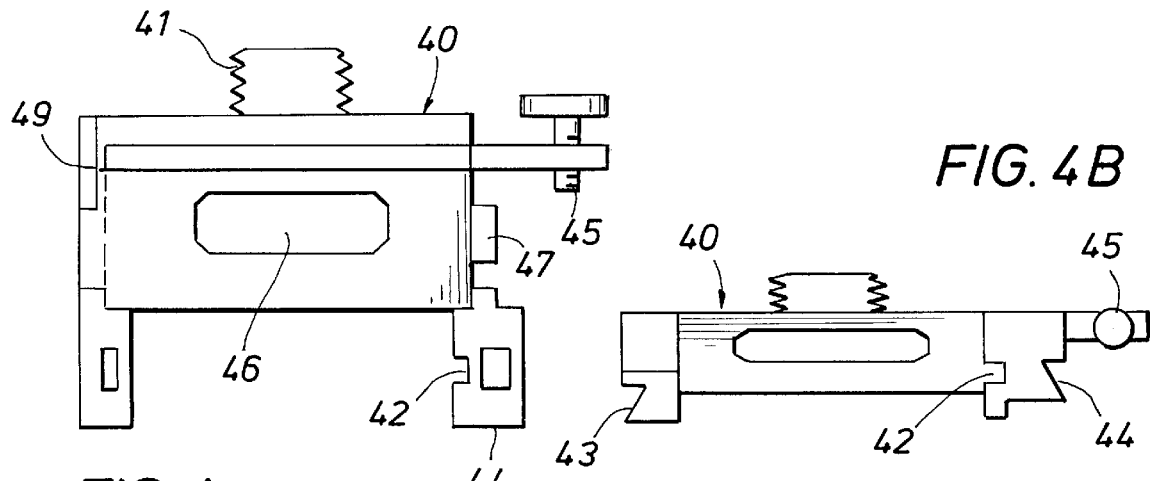
FIG. 4B
FIG. 4
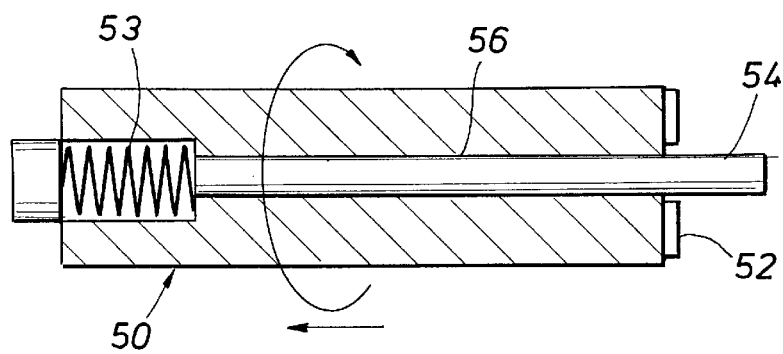
FIG. 5
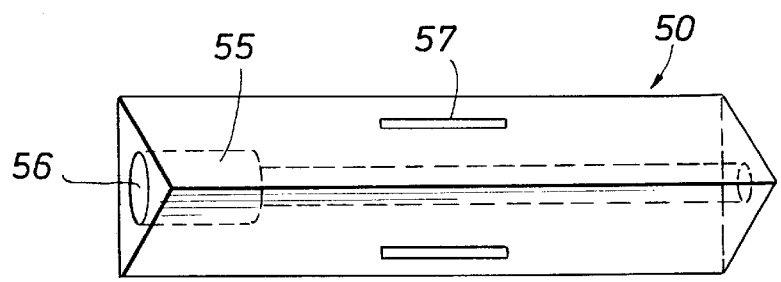
FIG. 5A

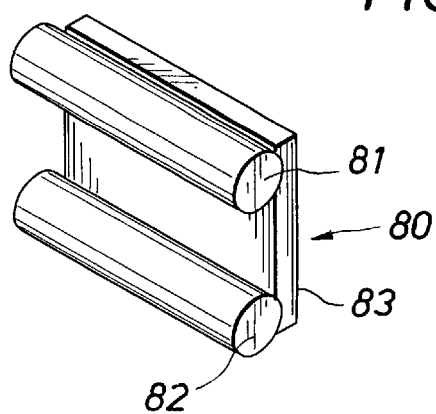
FIG. 8
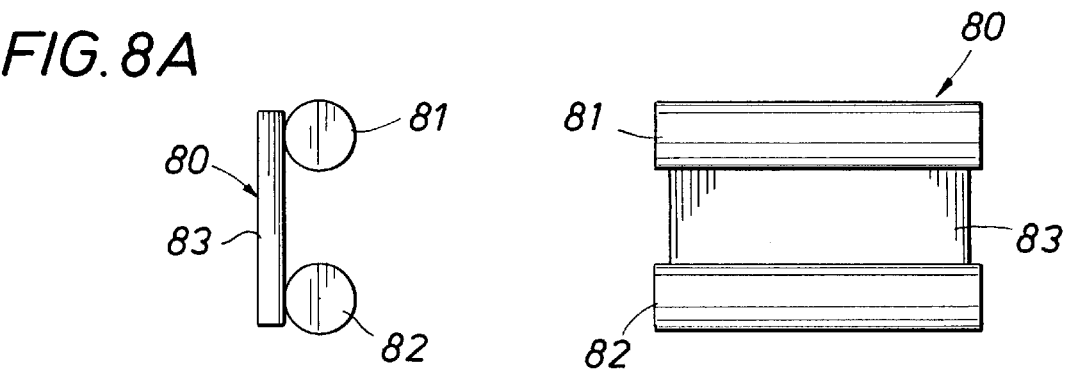
FIG. 8A
FIG. 8B
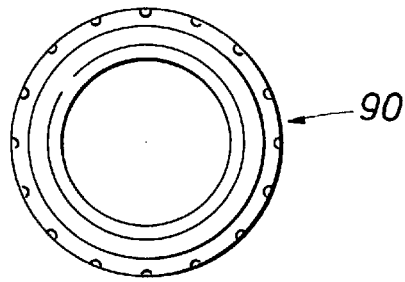
FIG. 9
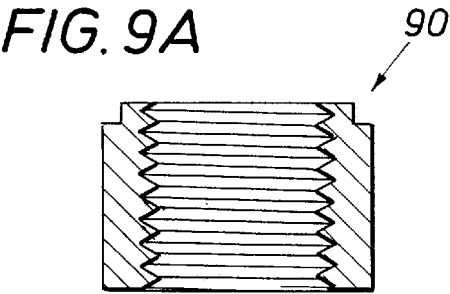
FIG. 9A
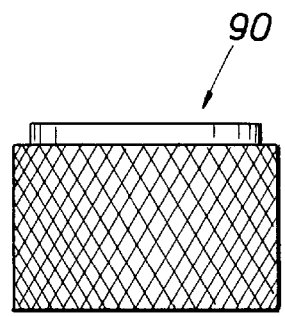
FIG. 9B FIG. 10A
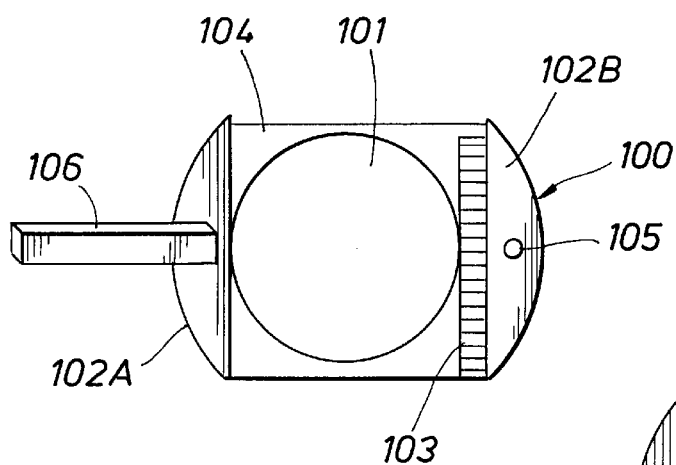
FIG. 10B
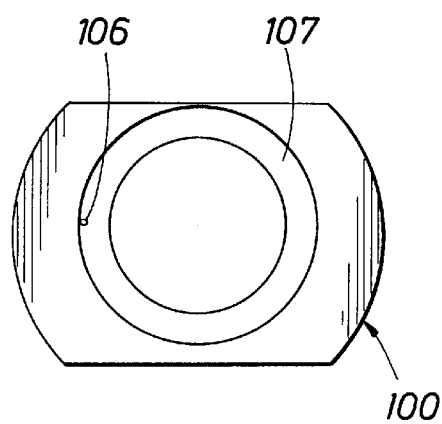
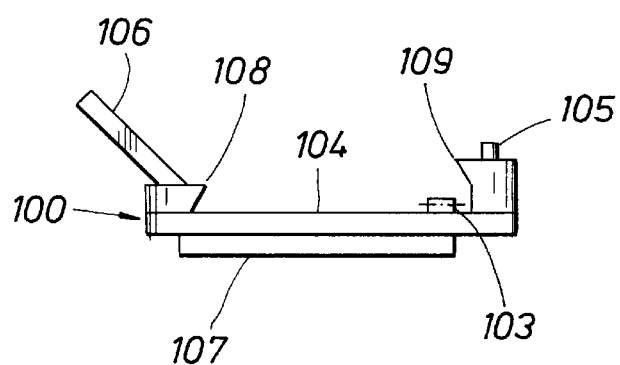
FIG. 10C
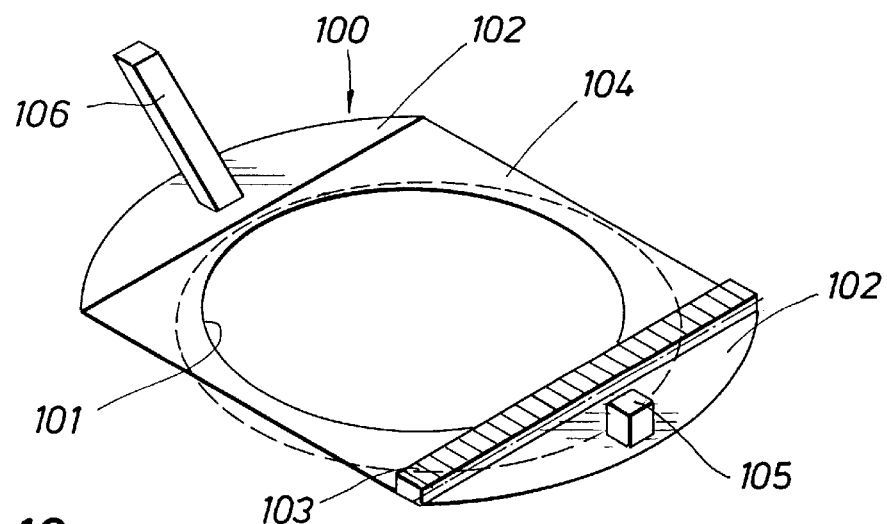
FIG. 10

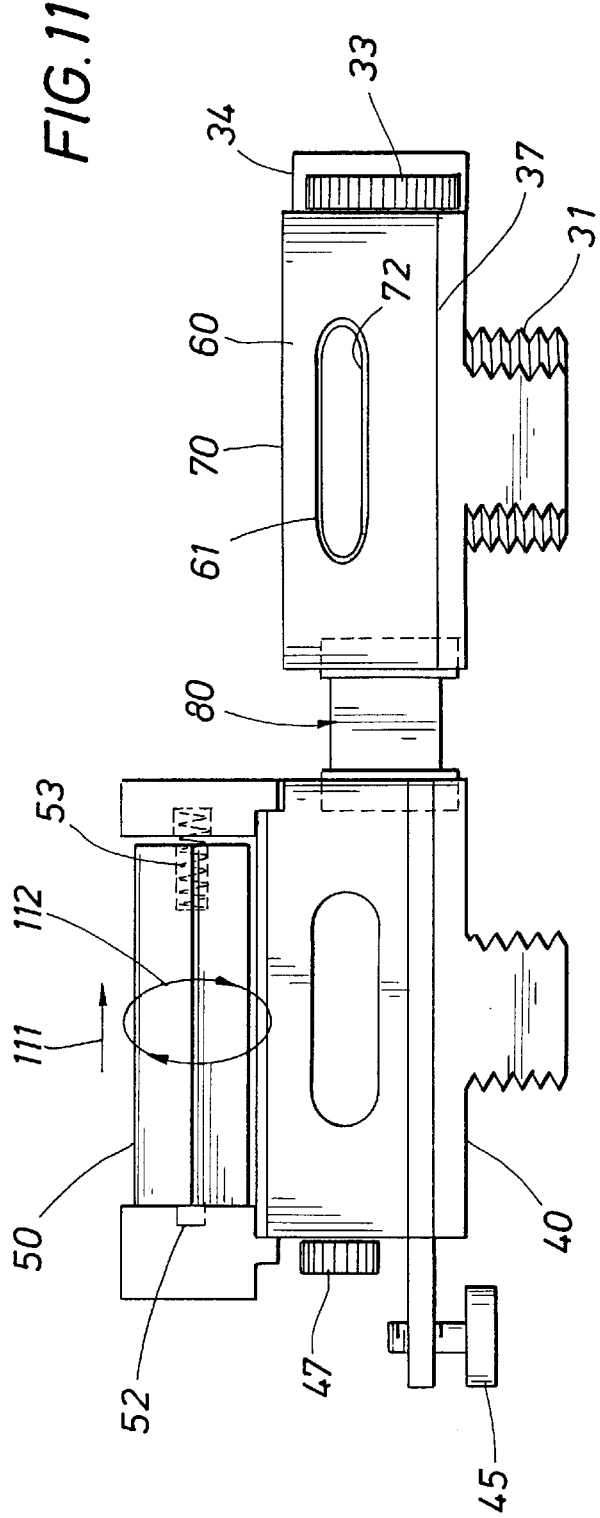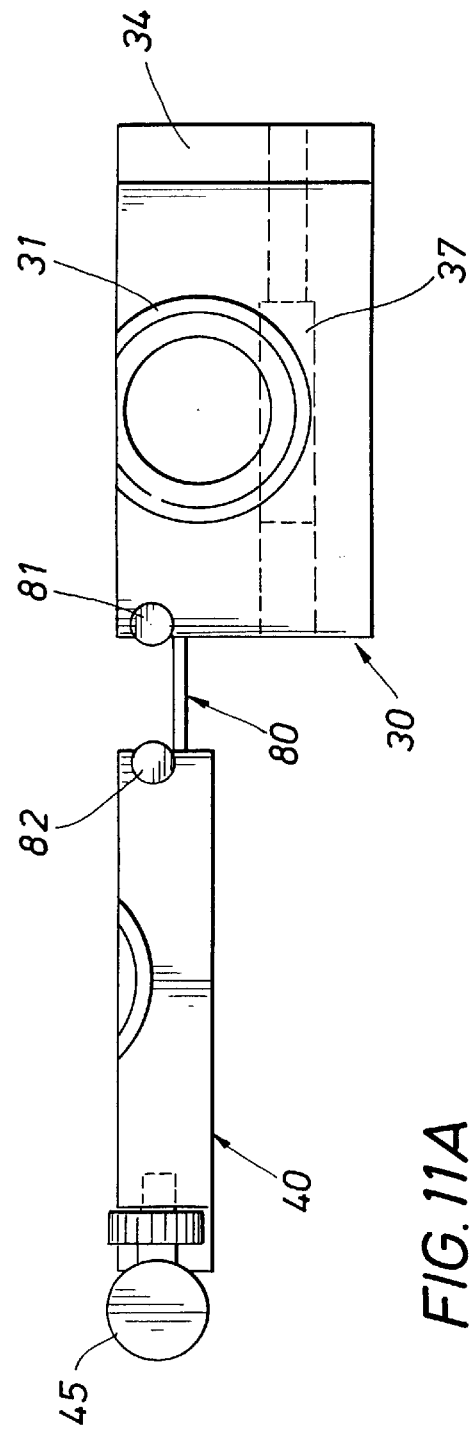

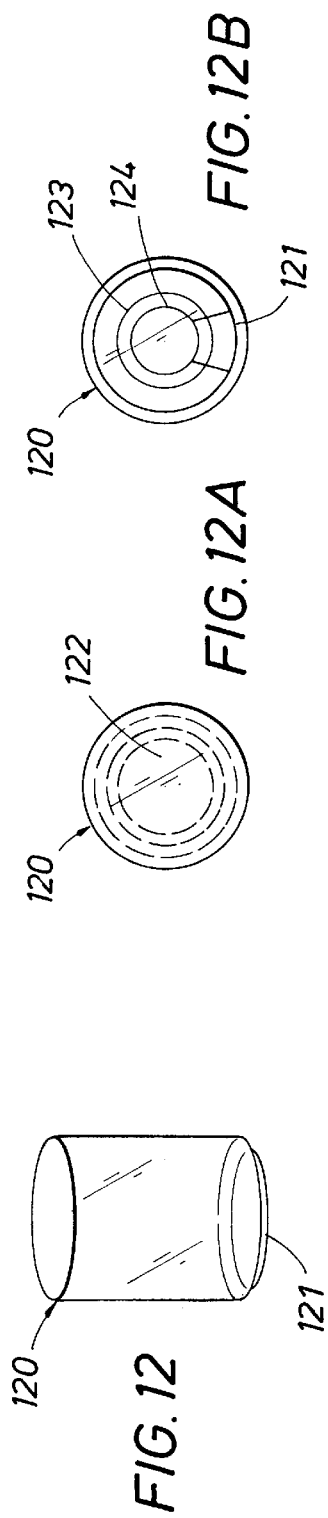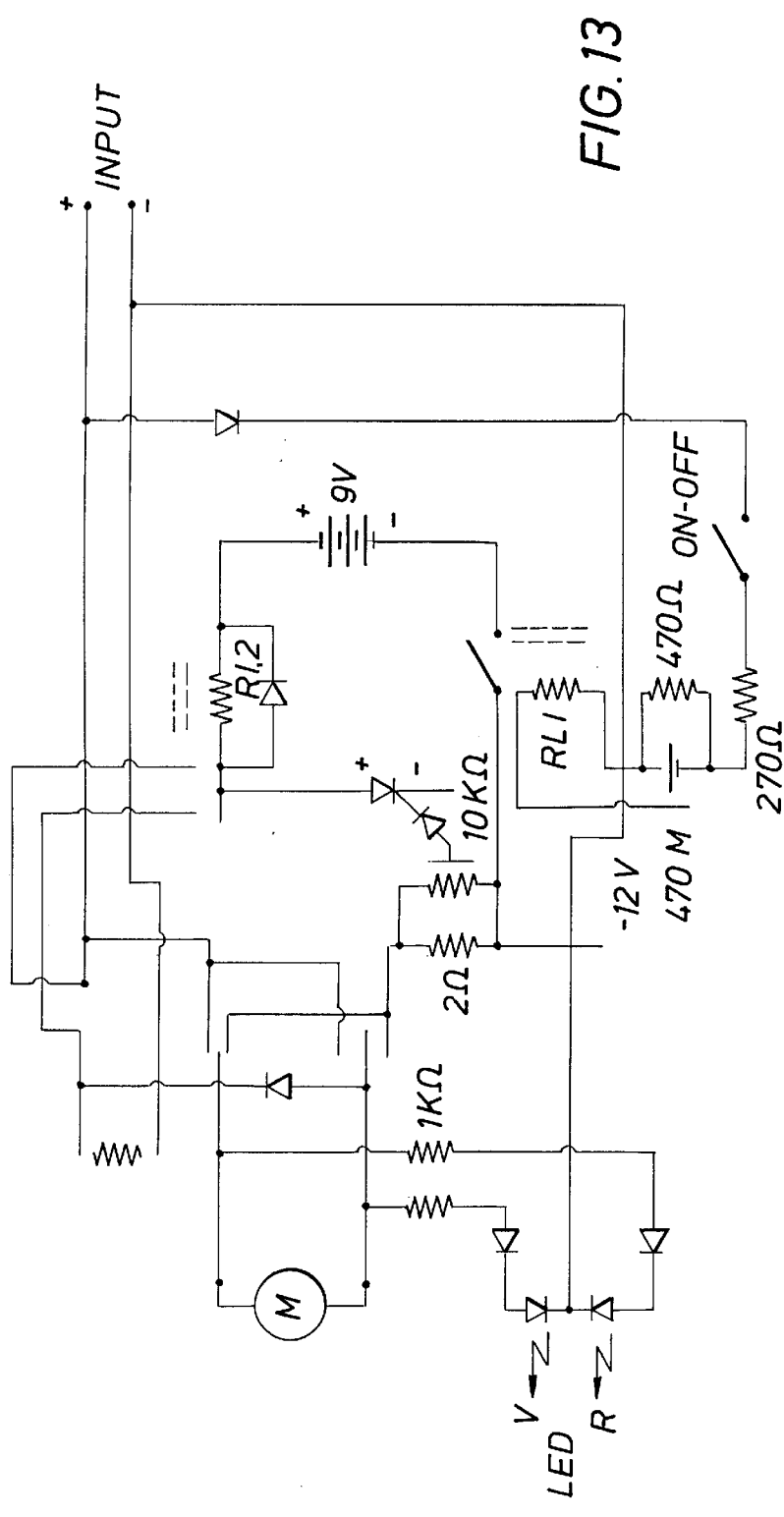
FIG.12  FIG.12A  FIG.12B  FIG.13

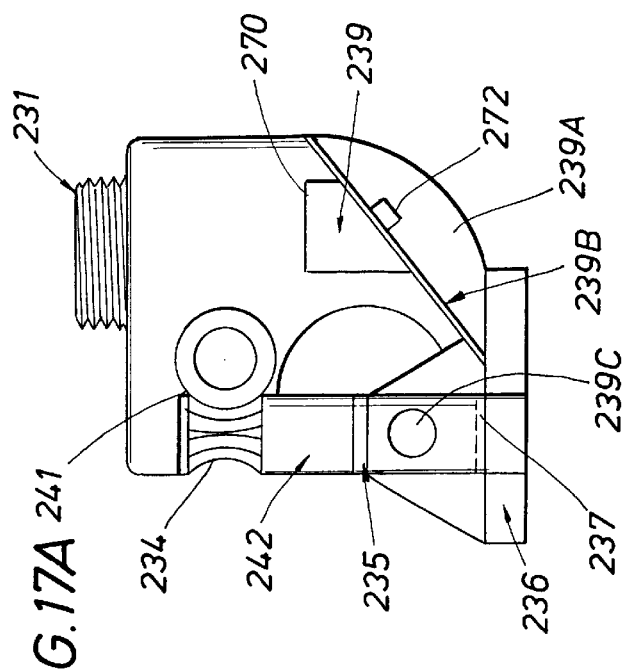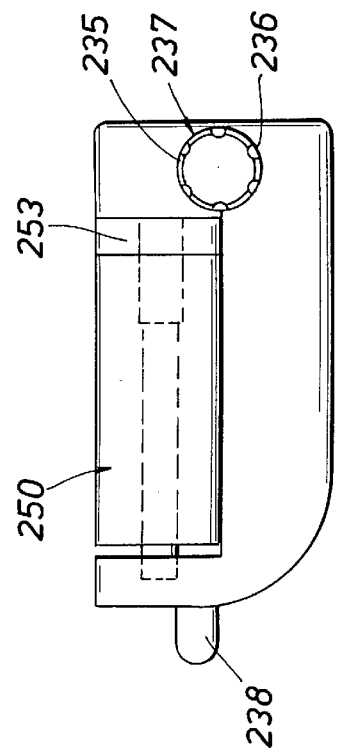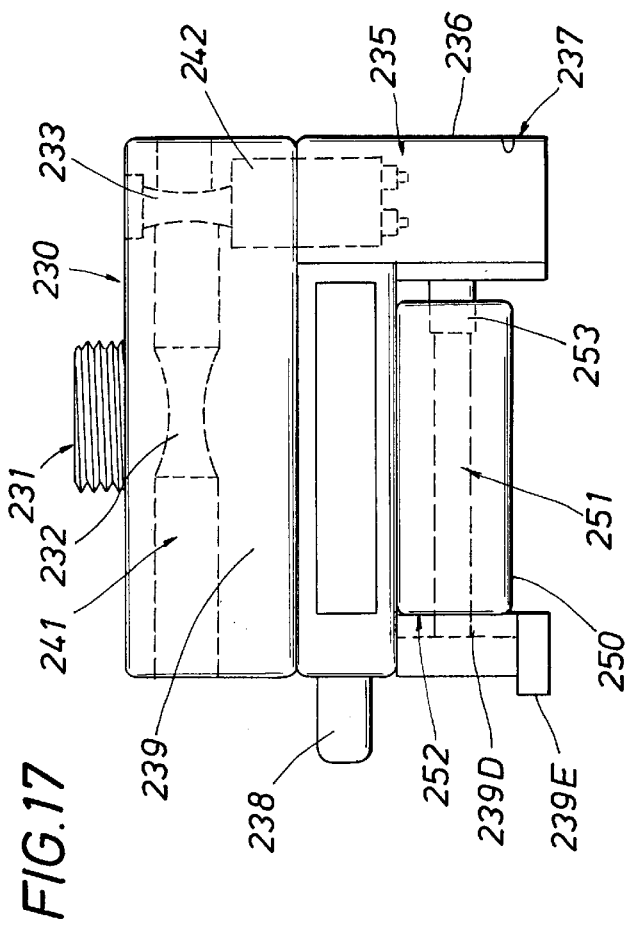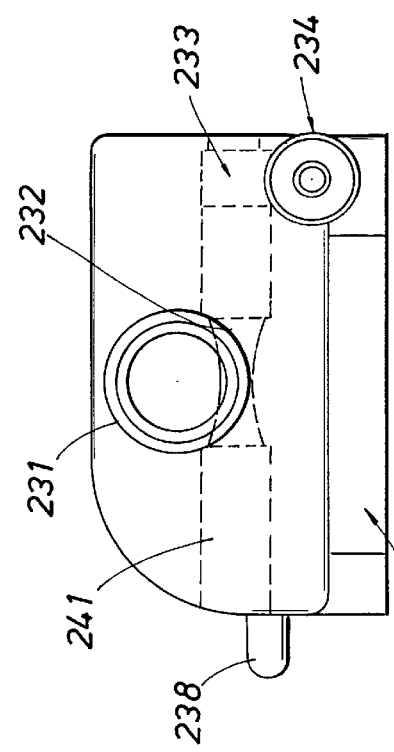

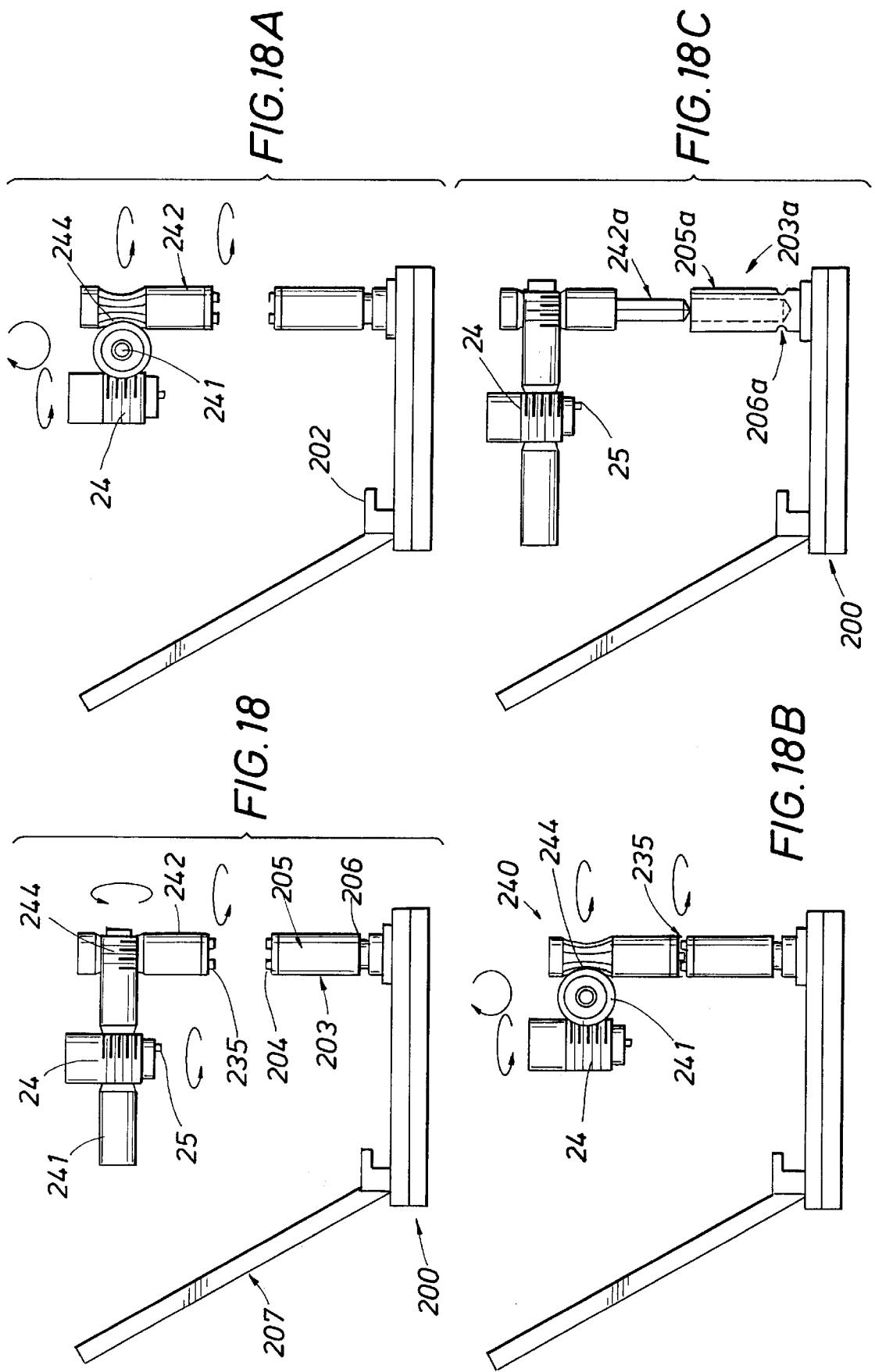

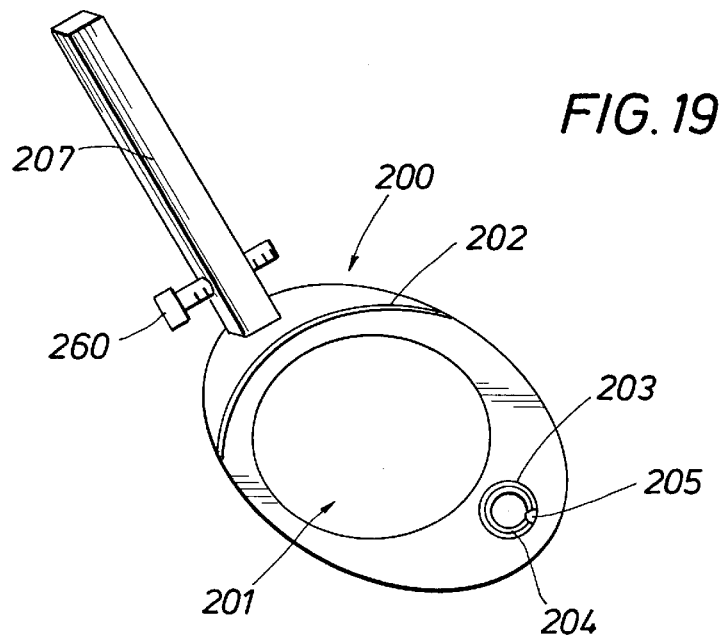
FIG. 19
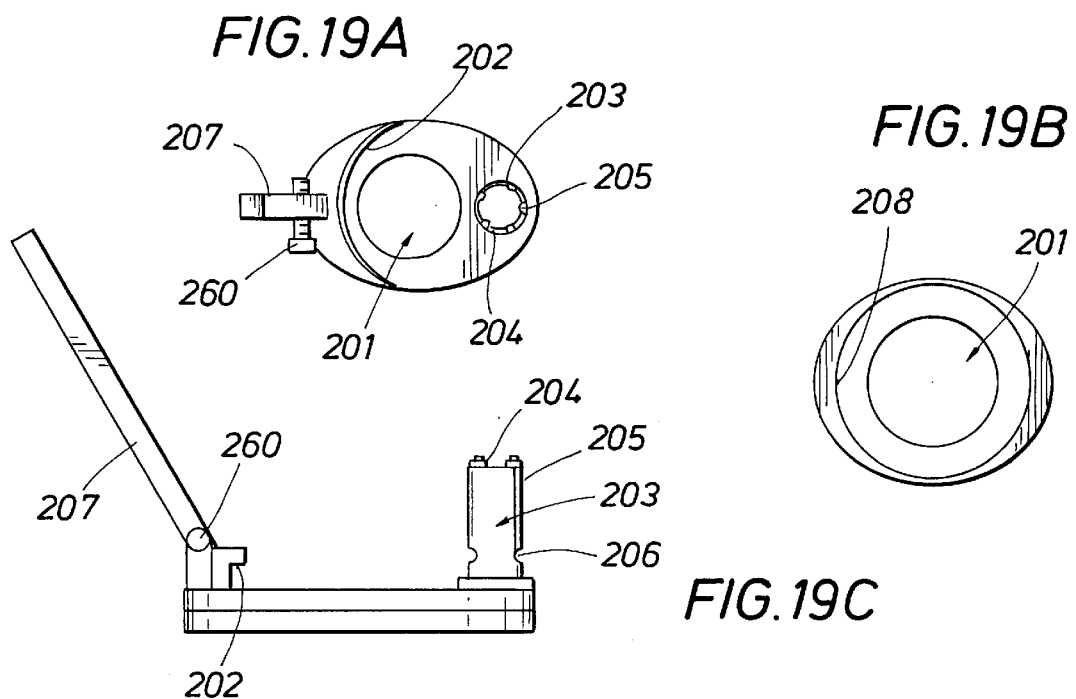
FIG. 19A
FIG. 19B
FIG. 19C
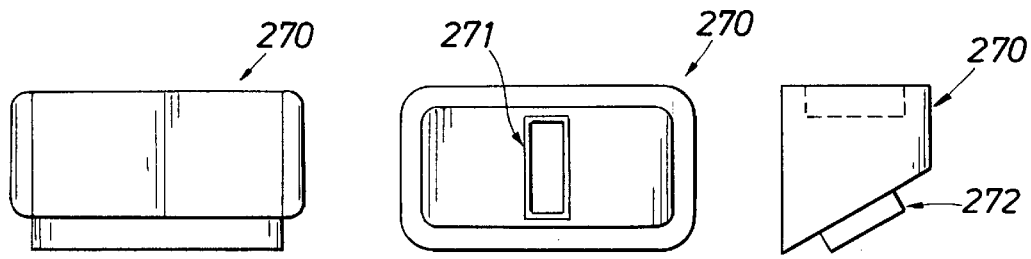
FIG. 20
FIG. 20A
FIG. 20B

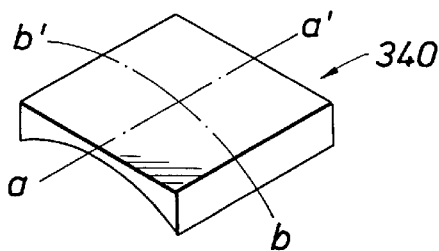
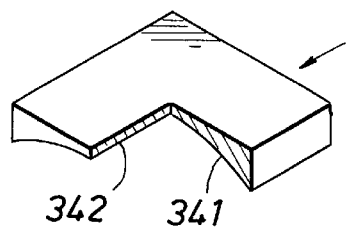
FIG. 29　　　　　　　　　　FIG. 29A
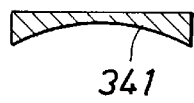
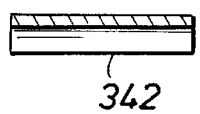
FIG. 29B　　　　　　　　　　FIG. 29C
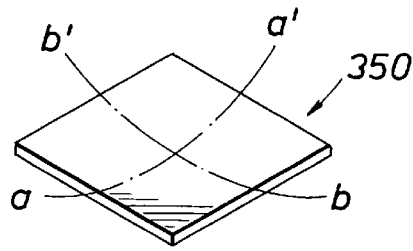
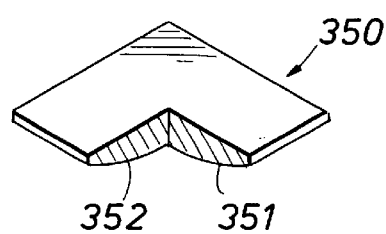
FIG. 30　　　　　　　　　　FIG. 30A
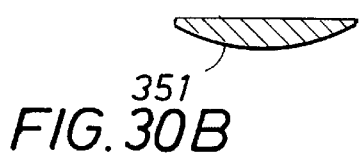
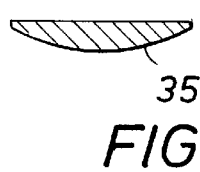
FIG. 30B　　　　　　　　　　FIG. 30C
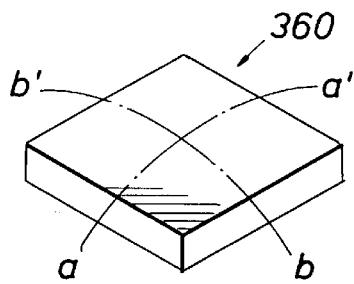
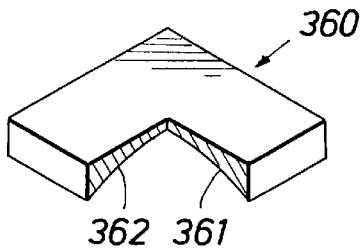
FIG. 31　　　　　　　　　　FIG. 31A
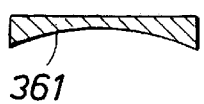
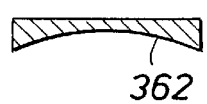
FIG. 31B　　　　　　　　　　FIG. 31C

MICROKERATOME AND METHOD OF PERFORMING CORNEAL RESECTIONS This application is a continuation-in-part of provisional application Ser. No. 60/056,775, filed Aug. 25, 1997 and U.S. application Ser. No. 08/772,698, filed Dec. 23, 1996 now abandoned.

BACKGROUND OF THE INVENTION

1. Field of the Invention

The present invention relates to medical instruments and methods for performing eye surgery to correct irregularities of the cornea. More particularly, the present invention relates to mechanical instruments known as microkeratomes, and related surgical methods for performing lamellar keratotomies.

2. The Related Art

The first microkeratome for performing corneal resections was developed in 1962 by one of the present inventors, Doctor Jose I. Barraquer, and is shown generally in FIG. 1A. This microkeratome includes a guide ring which is fixed to an ocular globe, or eyeball, with the aid of a partial vacuum applied through the ring. The guide ring immobilizes the ocular globe, maintains the tension of the globe, and regulates the diameter of the corneal resection. A portion of the microkeratome called a cutting head is supported within a channel in the guide ring for guided linear movement of the microkeratome across the ring by the surgeon. The cutting head carries a cutting blade that is oscillated by a motor-driven eccentric transverse the channel as the instrument is moved through the cutting path defined by the channel. The cutting head carries a removable, lower planar member that compresses the ocular globe ahead of the oscillating blade, to permit the blade to cut a lamella having a lower surface that is parallel to the surface of the cornea that is compressed by the planar member. The planar member is interchangeable with similar planar members of differing thicknesses, so as to vary the thickness of the resectioned corneal "disk."

Numerous variations on the Barraquer microkeratome have been made since 1962, including the apparatus that is the subject of U.S. Pat. No. 4,662,370 assigned to Carl-Zeiss-Stiftung of Germany. The '370 patent describes a microkeratome having interchangeable inserts with convex, concave, and planar surfaces that engage and compress the cornea for producing a corneal resection of predetermined form and curvature. The inserts are set within a stationary planar member that is fixed to the guide ring. The cutting blade is moved through a cutting path parallel to the planar member defined by a gap between the planar member and the guide ring, and oscillates transverse the path.

While apparently effective to permit resections of corneal lenticula, the apparatus of the '370 patent lacks means for controlling, or automating the rate of movement by the cutting head across the guide ring, and is therefore prone to binding up in the corneal tissue, or otherwise producing imprecise resections under unsteady progress by the surgeon's hand. Furthermore, there is no apparent means for changing the depth or thickness of the corneal resection. Also, this apparatus is limited to use in lamellar keratectomies (excision of a corneal section), as opposed to lamellar keratotomies (incision through the cornea).

The problem of controlled movement across the guide ring has been addressed by the instrument described in U.S. Pat. No. 5,133,726, which has been reissued as Re 35,421, to Luis A. Ruiz and Sergio Lenchig G. The '726 and '421 patents disclose a microkeratome, shown in FIG. P2, having a gear transmission assembly for moving the instrument through the cutting path at a controlled rate of speed. The gears are driven by the same motor that drives the cutting blade and engage a track atop the guide ring. Thus, the automated transmission system is an improvement over the instrument of the '370 patent, but in practice it has been found that the weight of the motor in the instrument produces a large moment through the handle of the device. This moment, coupled with the forward positioning of the gear that engages the guide ring track, causes the rear surface of the cutting head to bind in its engagement with the guide ring. At best, this results in uneven travel by the instrument during the surgery and unnecessary pressure fluctuations within the eye. At worst, such binding can cause irregular cutting of the cornea that produces leucoma, or the induction of an astigmatism.

The relatively recent technological development of intrastromal refractive surgery led to the creation of instruments and methods for performing incomplete lamellar temporo-nasal keratotomies, which leave a peripheral residue of corneal tissue uncut to act as a "nasal hinge." The nasal hinge permits the corneal disk to be lifted for exposure and carving of the stromal layer, such as by a laser. The use of a laser to perform stromal carving in association with an incomplete lamellar keratotomy is referred to as "Laser Intrastromal Keratomileusis" ("LASIK").

In similar fashion to the original Barraquer device, the microkeratome of the '726 and '421 patents include a forward planar member in the lower portion of the cutting head that is interchangeable with similar planar members of varying thicknesses. For the planar member to be interchangeable, however, a slotted portion of the cutting head extends substantially forward of the cutting blade to receive the planar member. This, and the fact that the transmission gears are positioned outside the cutting head, result in a fairly large surface area, or "footprint" for the instrument. The large footprint restricts the manner in which the microkeratome can be used, and generally requires that it be moved across the cornea from the temporal region adjacent the eye, producing the vertical nasal hinge when performing incomplete lamellar keratotomies. The vertical nasal hinge has at least two deficiencies. First, the corneal disk resulting from the LASIK, or other procedure, will be vertically displaced after surgery, and/or pleated to some extent by the opening and closing of the upper eyelid. Second, the formation of a vertical nasal hinge on the corneal disk increases the likelihood of accidental ablation of the hinge during the correction of an astigmatism, which is typically performed with vertical cutting motions across a major diameter of the cornea.

The large surface area of the planar member, or plaque, described in the '726 patent is designed to substantially compress the entire cornea at any one time. Such action produces unnecessarily high intraocular pressure, which unduly stresses the eye and could result in complications during surgery. Furthermore, the interchangeable planar members lack means for indicating the thickness of the resection to be provided by the respective members. This creates the possibility that a planar member having the wrong thickness will be inserted into the cutting head. In such an event, the instrument might perform an exaggerated cut and perforate the ocular globe, causing serious consequences.

In response to the shortcomings described herein, it is an object of the present invention to provide an improved microkeratome wherein the cutting head is moved across the cornea by sweeping pivotal motion relative to a fixed point on a guide ring positioned on a patient's eye.

It is a further object that such pivotal motion be induced automatically by the engagement of gears with an output shaft that induces rotation about a pivot post connected to a guide ring at the fixed point.

It is a further object to provide an improved microkeratome having an adjustable float head, or plaque, connected to the cutting head for varying the thickness of corneal resections without having to disassemble or replace a component of the instrument.

It is a further object that the adjustable float head be provided with indicia for indicating the selected depth of cut, whereby inadvertent mistakes regarding the thickness of the resection are less likely to occur.

It is a further object of the present invention that the float head exhibit a small surface area to permit corneal resections without the cutting head or float head exceeding the rim of the guide ring. In this manner, oblique and lower-upper resections of the cornea can be performed during a lamellar keratotomy, whereby the risk of inadvertent ablation of the corneal hinge during an astigmatic correction, as well as the extent of fold and displacement of the corneal disc generated by the sweeping of the upper eyelid, are reduced.

It is a further object that the float head impart only the minimum pressure upon the ocular globe that is necessary to compress the cornea for a uniform resection.

It is a further object that the transmission gears be positioned inside the side walls of the cutting head to minimize the surface area of the instrument, whereby a superior corneal hinge lying in the upper region of the cornea can be produced.

It is a further object that, in a linearly driven embodiment of the present invention, the drive gear which engages the guide ring be positioned rearwardly with respect to the cutting head to eliminate any binding between the rear lower surface of the cutting head and the guide ring.

It is a still further object of the present invention to provide a means for selectively limiting the cutting range of the microkeratome through the cutting path defined by the guide ring, so as to regulate the formation of the corneal hinge during a lamellar keratotomy.

It is a still further object to provide means for automatically returning the microkeratome to its initial position on the guide rings, upon reaching the selected limit of the cutting range.

SUMMARY

The objects described above, as well as other objects and advantages, are achieved by a microkeratome for performing a lamellar keratotomy of an ocular globe. The microkeratome includes a guide ring for placement on the eyeball, or ocular globe such that the globe's cornea protrudes therethrough. Means are provided for temporarily fixing the guide ring to the ocular globe, so as to immobilize the eyeball relative to the instrument. A cutting blade suitable for corneal resections is carried in a cutting head over the guide ring through a cutting path defined by the guide ring. An adjustable float head, also generally known as a plaque, is connected to the cutting head for at least partially compressing the cornea ahead of the blade, so as to set the desired thickness of the corneal resection. Means are further provided for driving the cutting head and float head across the guide ring, whereby the blade cuts at least partially through the cornea to perform the lamellar keratotomy.

In a preferred embodiment of the present invention, the guide ring includes an upwardly extending pivot post, and the driving means includes an output shaft that extends downwardly through the cutting head for engagement with the pivot post, to constrain the output shaft against rotation relative to the pivot post. The driving means further includes means for applying a torque to the output shaft within the cutting head, whereby the cutting head and the float head are rotated about the output shaft by the driving means over the guide ring at a controlled speed. In this embodiment, the float head is not necessarily adjustable, and may be of a type that provides only a single predetermined shape and thickness of cut by the cutting blade.

In the preferred embodiment, the cutting head includes a hollow guide tube extending downwardly therefrom about the output shaft to guide the output shaft into engagement with the pivot post and to support the microkeratome above the guide ring on a plate at the base of the pivot post. In one instance, the pivot post and output shaft each include opposing complementary teeth means for axial engagement with one another. The guide tube includes a pin extending radially inwardly from its inner surface, and the pivot post includes a groove extending axially along the outer surface thereof. The pin fits into the groove to ensure that the teeth of the output shaft are properly aligned for engagement with the teeth of the pivot post.

Alternatively, the hollow guide tube is used with a splined output shaft, and the pivot post is provided with a grooved opening complementing the splined output shaft.

The preferred embodiment of the microkeratome further includes stop means for limiting the range through which the blade is carried through the cutting path so as to define a corneal hinge during a lamellar keratotomy.

The cutting head of the microkeratome may be of a unibody construction, or may include upper and lower members connected by a hinge that permits the cutting head to be opened for accessing the blade and float head.

The driving means preferably includes means for inducing oscillatory motion in the blade that is transverse the cutting path.

The adjustable float head preferably includes a pair of substantially parallel support arms, and a float member having a triangular cross-section and three faces. The float is supported for rotation between the support arms about a journal that extends through the float. Each of the three faces are spaced at different distances from the journal, whereby the thickness of the corneal resection is varied by rotation of the float until the desired face is in position to compress the cornea. The float head is further provided with indicia for indicating the resection thickness provided by the selected face. The faces of the float may be planar, arcuate, oblique, or any combination thereof, whereby corneal lenticular resections can be performed by compressing the cornea with the appropriate face.

Means may be further provided for automatically reversing the driving means when the stop means limits the range of the blade. In this manner, the microkeratome is returned to the position along the guide ring at which the surgery was initiated.

In a second embodiment of the present invention, the guide ring includes track means that is engageable by a transmission means carried within the cutting head and driven by the driving means for moving the cutting head over the guide ring at a controlled speed. The transmission means of this embodiment is positioned substantially within the cutting head, whereby the microkeratome has a narrow width that permits it to make an upper-to-lower cut through the ocular globe without interference with a patient's facial structure. Stop means are provided for limiting the range through which the blade is carried through the cutting path so as to define a corneal hinge during an incomplete lamellar keratotomy, whereby the microkeratome is capable of defining a superior corneal hinge.

The objects set forth above are further achievable through a method of performing resections of corneal lenticula. A guide ring is first fixed to an ocular globe about the globe's cornea so that the cornea extends through and above the guide ring. A float head having an arcuate or oblique surface is then moved over the guide ring so as to compress the cornea with the arcuate or oblique surface into a shape that complements the surface. A cutting blade is then moved through a plane across the guide ring so as to resect a corneal lenticula. The float head may be held stationary once it has compressed the cornea prior to the movement of the blade, or the float head may be moved with the blade while maintaining contact with the cornea.

When it is desired to create a corneal hinge for intrastromal surgery, the cutting blade is moved a predetermined distance substantially, but not completely across the portion of the cutting plane that intersects the cornea. The movement of the cutting blade is restricted by an adjustable stop means, whereby the extent of hinge width formed on the corneal cap is adjustable. The cutting blade is then moved back across the guide ring to its original position, so that the resulting corneal cap can be folded and secured over its hinge. At that point, the corneal stroma is resected as deemed appropriate, preferably by a laser.

The present invention further contemplates another method of performing corneal resections for a lamellar keratotomy. This method includes the steps of fixing a guide ring to an ocular globe about the globe's cornea so that the cornea extends through and above the guide ring, and pivoting a float head across the guide ring about a fixed point on the guide ring, through the application of torque at the fixed point, so that the float head sweeps in an arcuate path and compresses the cornea into a shape that complements the float head's lower surface. A cutting blade is pivoted behind the float head about the fixed point so that the blade sweeps in an arcuate path through a plane beneath the float head's lower surface so as to perform a corneal resection.

When adding the step of stopping the cutting blade short of cutting completely through the cornea so as to define a corneal hinge, this method is useful to produce a corneal hinge lying in the superior region of the cornea.

BRIEF DESCRIPTION OF THE DRAWINGS

In the drawings, wherein like reference characters are used throughout to describe like parts:

FIG. 1 is an isometric view of a microkeratome and the present invention;

FIGS. 2, 2A, and 2B are lateral, transparent lateral, and frontal projections, respectively, of the driving means and eccentric for inducing oscillatory motion in the cutting blade, in accordance with the present invention;

FIGS. 3, 3A, 3B, and 3C are inferior, rear, and lateral projections, respectively, of the superior portion of the cutting head utilized in the embodiment of FIG. 1;

FIGS. 4, 4A, and 4B are superior, lateral, and frontal projections, respectively, of the inferior portion of the cutting head utilized in the embodiment of FIG. 1;

FIGS. 5, 5A, 5B, 5C, and 5D are frontal, superior perspective, and lateral projections, respectively, of a float head in accordance with the present invention;

FIGS. 8, 8A, and 8B are perspective, lateral, and superior projections, respectively, of the cutting head hinge in accordance with the cutting head of FIGS. 3 and 4;

FIGS. 9, 9A, and 9B are frontal, lateral section, and lateral projections, respectively, of the threaded nut that couples the superior and inferior portions of the cutting head, as further indicated in FIG. 11;

FIG. 10 is an isometric projection of the guide ring assembly;

FIGS. 10A, 10B, and 10C are superior, inferior, and lateral projections, respectively, of the guide ring assembly;

FIGS. 11 and 11A are superior and rear projections, respectively, of the cutting head utilized in the embodiment of FIG. 1 in an opened position, revealing the cutting blade and float head;

FIGS. 12, 12A, and 12B are lateral, superior, and inferior projections of a regulating tool for setting the size of the corneal cap resulting from the use of the present invention;

FIG. 13 is an electrical schematic of an automatic setback circuit used to return the microkeratome to its starting position upon completion of the corneal incision;

FIGS. 17, 17A, 17B, and 17C are respective frontal, lateral, superior, and inferior projections of a portion of the drive mechanism and cutting head utilized by the preferred embodiment of the present invention, shown partially transparent;

FIGS. 18, 18A, and 18B are respective frontal disengaged, lateral disengaged, and lateral engaged projections of the gear assembly utilized by the drive mechanism of the preferred embodiment;

FIG. 18C is a lateral disengaged projection of an alternative gear assembly according to the preferred microkeratome of FIG. 15;

FIGS. 19, 19A, 19B, and 19C are respective isometric, superior, inferior, and lateral projections of the guide ring assembly according to the preferred embodiment of the present invention;

FIGS. 20, 20A, and 20B are respective frontal, superior, and lateral projections of a blade holder in accordance with the preferred microkeratome of FIG. 15;

FIG. 29 is an isometric projection of a flat-concave plaque and its two main meridians;

FIG. 29A is a longitudinal and cross-sectional partial cut;

FIG. 29B is a cross-sectional cut of the meridian a–a';

FIG. 29C is a cross-sectional cut of the meridian b–b';

FIG. 30 is an isometric projection of a biconvex plaque and its two main meridians;

FIG. 30A is a longitudinal and cross-sectional partial cut for better visualization;

FIG. 30B is a cross-sectional cut of the meridian a–a';

FIG. 30C is a cross-sectional cut of the meridian b–b';

FIG. 31 is an isometric projection of a biconcave plaque and its two main meridians;

FIG. 31A is a longitudinal and cross-sectional partial cut;

FIG. 31B is a cross-sectional cut of the meridian a–a';

FIG. 31C is a cross-sectional cut of the meridian b–b';

DETAILED DESCRIPTION OF THE PREFERRED EMBODIMENTS

The Linearly Driven Embodiment of the Microkeratome

FIGS. 1–14B illustrate one embodiment of microkeratome 10 for performing a lamellar keratotomy or a lamellar keratectomy of an ocular globe, in accordance with the present invention. The instrument is suitable to perform surgery of myopia (nearsightedness), hyperopia (farsightedness), astigmatism, and lamellar corrections in general such as for ectasia (corneal dilation) and presbyacusis (corneal stiffening due to aging), and is particularly well-suited to perform cuts other than temporo-nasal, such as bottom, upper, and oblique cuts.

Figure 1A:
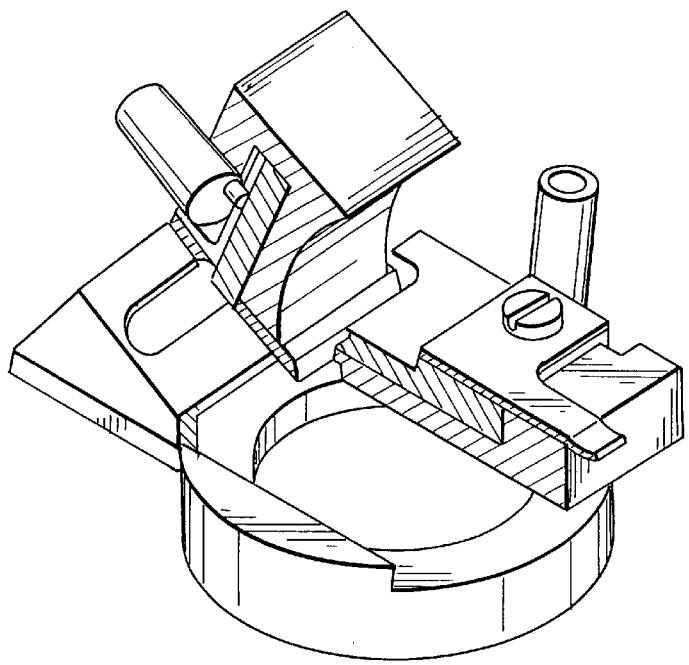
FIG. 1A is an isometric view, partially in section, of the original Barraquer microkeratome.
Figure 1B:
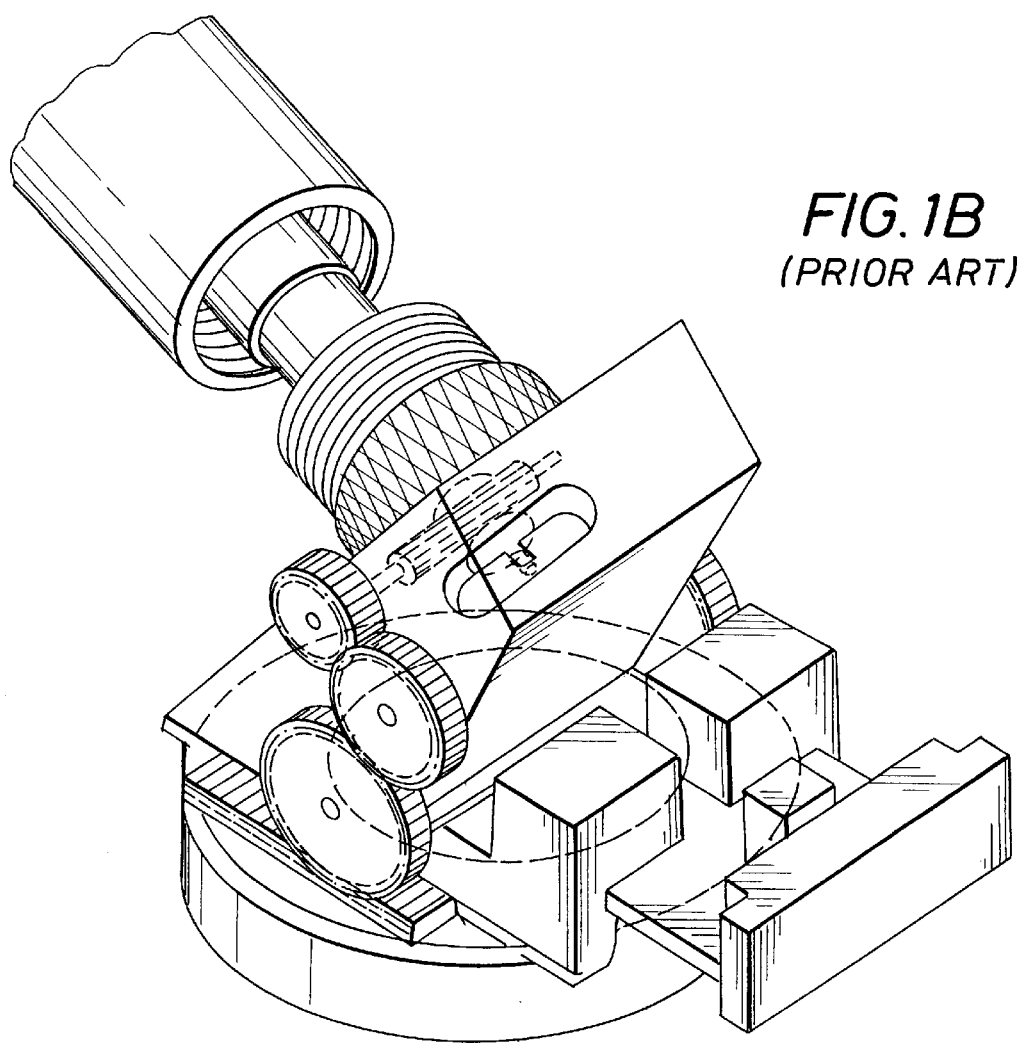
FIG. 1B is an isometric view of a prior art microkeratome described in U.S. Pat. Nos. 5,133,726 and Re 35,421.

This embodiment of the microkeratome includes three primary components, as shown generally in FIGS. 1 and 1E. First, there is a driving means assembly 20 that includes a speed reduction system and an eccentric pin assembled in a single unit. Second, a cutting head assembly includes hinged superior and inferior portions 30, 40 that carry a gear transmission means 32, 33, 47, a blade assembly, stop means 45, and float head assembly 50. Third, guide ring assembly 100 includes range limiter 105.

Microkeratome 10 further employs two independent components for its function. Thus, the microkeratome makes use of a regulating lens/hinge meter tool, and an independent unit (not shown) containing a power source with or without an incorporated motor, a suction pump, and an automatic setback electronic circuit.

FIGS. 2, 2A, and 2B illustrate driving means housing 20 and its components in greater detail. The driving means allows for two operation speeds, one for the cutting blade that is equal to that of the drive motor (not shown), and the other being reduced to a controlled speed for advance of the instrument during surgery. An electric drive motor, or similar means provides the torque necessary for rotating input shaft 21. Shaft 21 frictionally engages and transmits a torque to shaft 22, which terminates outside housing 20 in small eccentric projection or pin 25. Eccentric pin 25 engages slot 71 of blade holder 70, shown in FIG. 7, through threaded portion 31 of superior cutting head portion 30, seen in FIG. 3, to transmit an oscillatory motion to blade 60 that corresponds to the speed of the motor. This relationship is discussed further below.

Shaft 22 also rotates threaded portion 24 thereof, which ultimately drives the gear transmission system in the cutting head. More particularly, threaded portion 24 engages worm gear 37 mounted on shaft 32S, shown in FIGS. 3–3C, which terminates at one end thereof in gear 32. The shaft is mounted for rotation in superior portion 30 of the cutting head. Gear 32 engages larger diameter gear 33, which in turn engages small diameter gear 47, the latter being mounted for rotation in inferior portion 40 of the cutting head, as seen in FIG. 1D. Together, the gears form a transmission means that cooperates with the above-described driving means for engaging and driving the cutting head in a linear path across guide ring assembly 100 at a reduced speed relative to the motor speed, as shown in FIG. 11E. More particularly, small diameter gear 47 engages gear track 103 on guide ring 104 for moving the cutting head over the guide ring assembly at the controlled rate of speed, as shown in FIG. 11E. In this manner, the cutting blade (described below) cuts at least partially through the cornea to perform the desired lamellar keratotomy.

The cutting head of linearly driven microkeratome 10 contains cylindrical cavity 38 that is partially formed by threaded portion 31 of superior cutting head portion 30, and partially formed by threaded portion 41 of inferior cutting head portion 40, as shown in FIGS. 3, 4, and 11. Cylindrical cavity 38 terminates in elongated slot 35 which contains blade holder 70, shown in FIGS. 7–7B, for slidable movement therein as explained further below.

Referring again to FIG. 4, as well as FIGS. 4A and 4B, inferior portion 40 of the cutting head includes a pair of ski-like gliders 43, 44 of different heights, each having a 60° dovetail for engagement with complementary grooves 108, 109 of guide ring assembly 100, as shown in FIG. 10C. Inferior portion 40 engages superior portion 30 along a plane that makes a 30° angle with the planes in which gliders 43, 44 lie, as shown particularly in FIG. 4A.

Figure 7A:
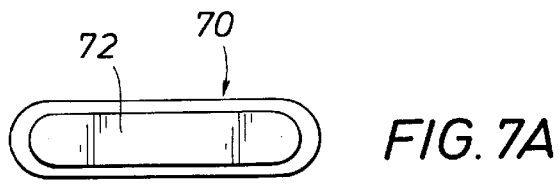
FIGS. 7, 7A, and 7B are frontal, superior, and lateral projections, respectively, of the blade holder utilized in the embodiment of FIG. 1.
Figure 7:
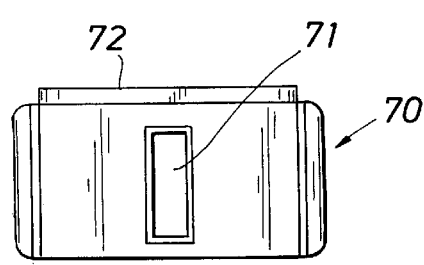
Figure 7B:
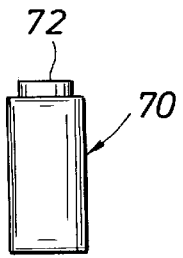

Inferior portion 40 is equipped with elongated slot 46, which loosely receives blade holder 70 when the superior and inferior portions of the cutting head are brought together. Blade holder 70 exhibits an elongated cross-section similar to the shape of slots 46 and 35, but is somewhat smaller to allow for lateral movements of the blade holder within the slots. Blade holder head 72 is also of the same shape, but is reduced in size from blade holder body 70, as seen in FIG. 7A.

Figure 6B:
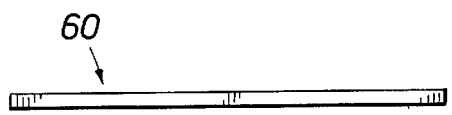
FIGS. 6, 6A, and 6B are frontal, lateral, and superior projections, respectively, of the cutting blade.
Figure 6:
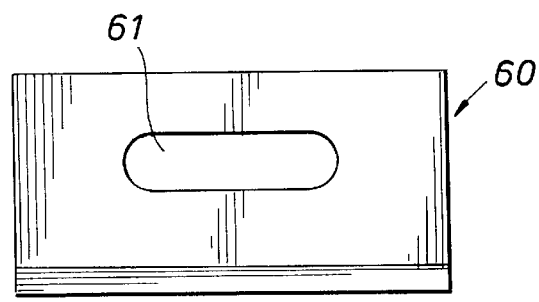
Figure 6A:
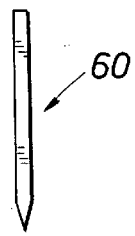
Figure 14:
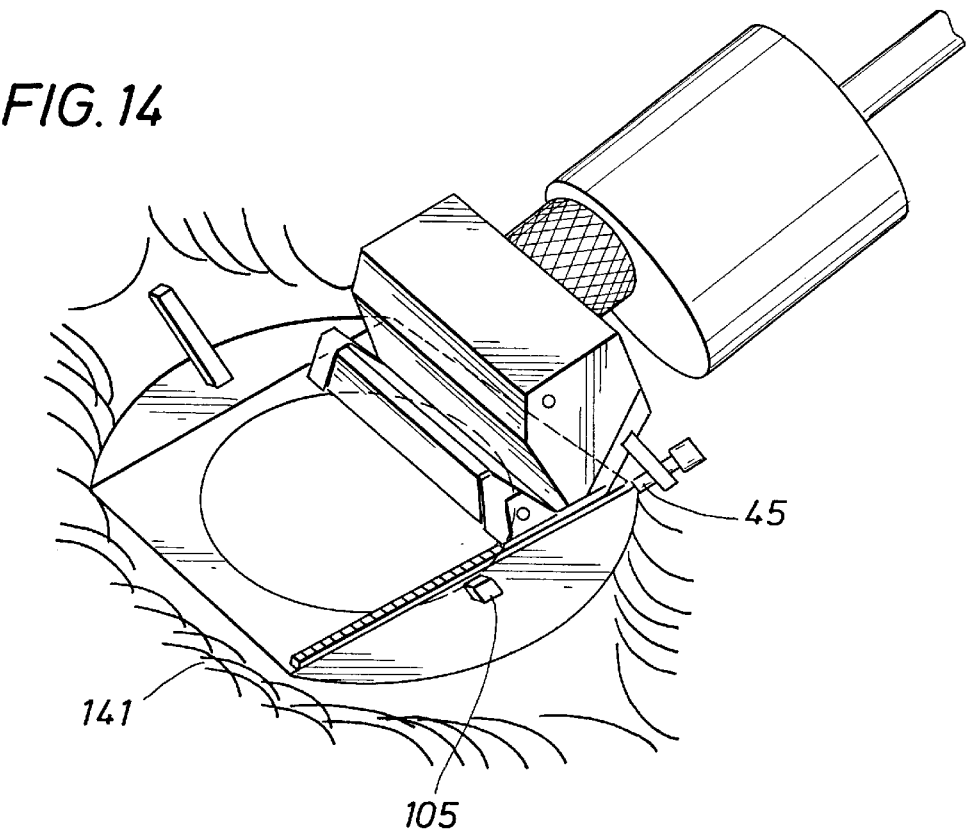
FIGS. 14 and 14A are isometric projections of the microkeratome embodied in the FIGS. 1 and 11E engaging the guide ring at the beginning and the end, respectively, of a vertically oriented corneal resection.
Figure 14A:
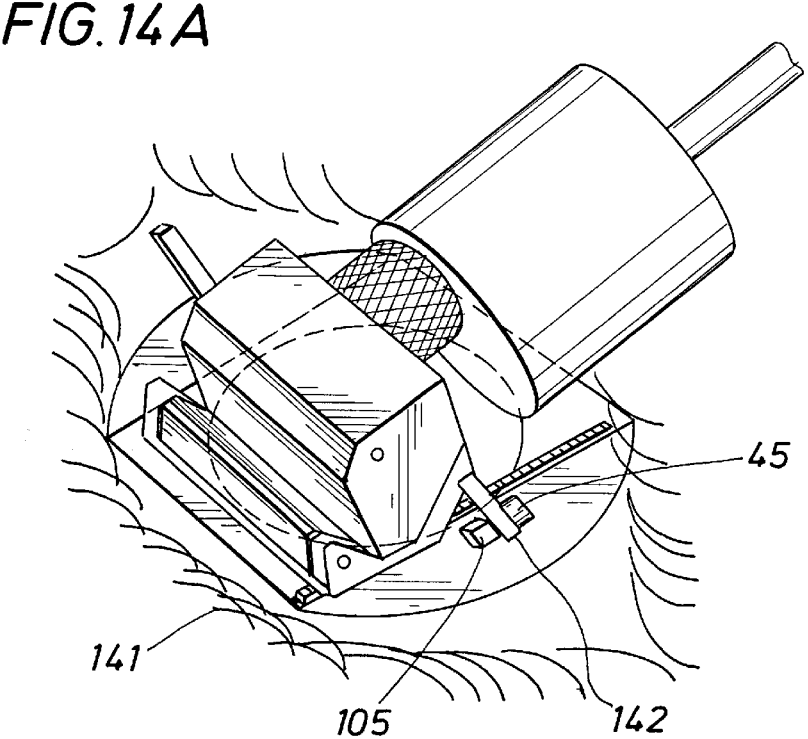
Figure 14B:
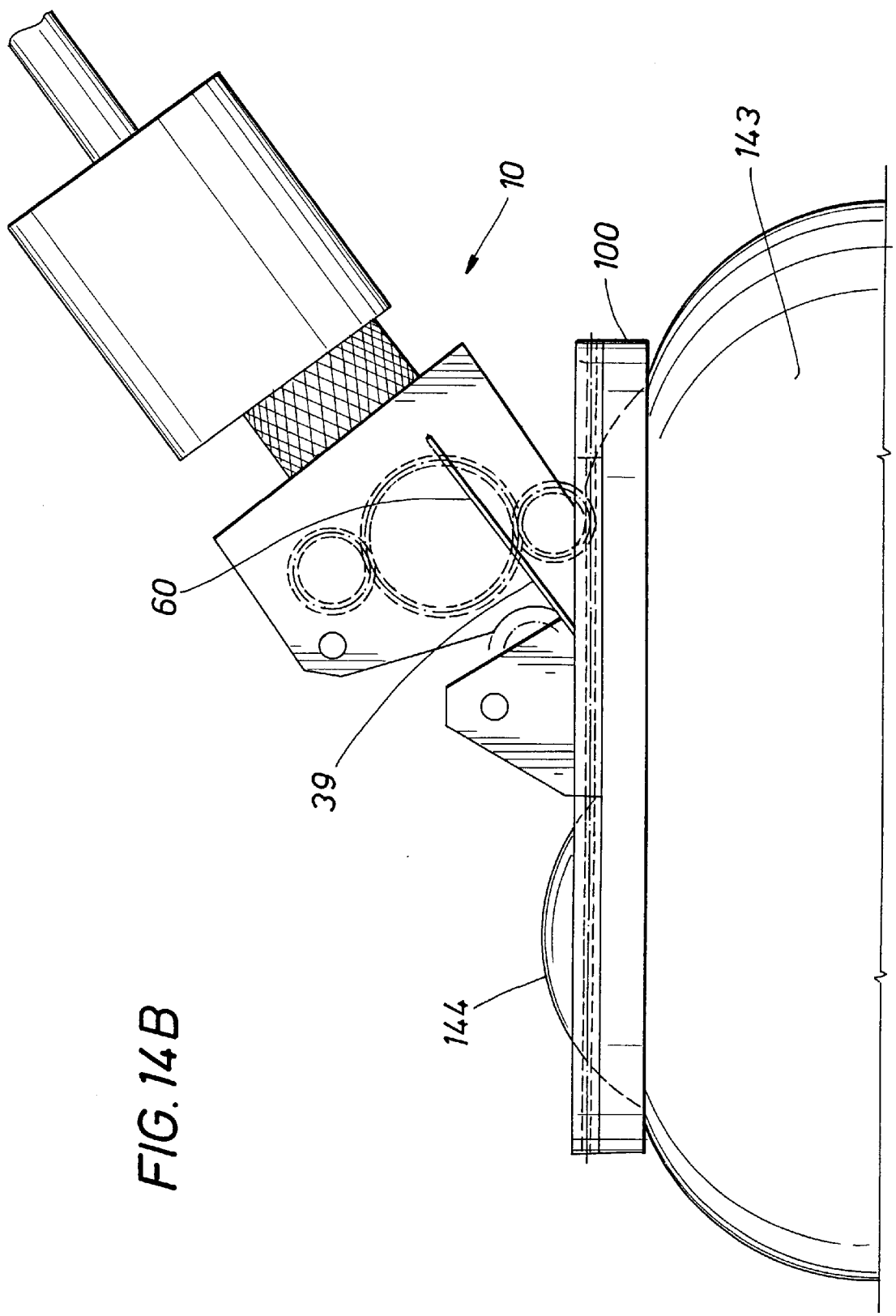
FIG. 14B is a lateral projection, partially transparent, of the microkeratome of FIGS. 1 and 11E engaging the guide ring during a corneal resection.

Cutting blade 60, illustrated in FIG. 6, is rectangular and includes elongated slot 61 that closely fits over head 72 to mount the blade to the blade holder within the cutting head. As mentioned above, blade holder 70 has vertical rectangular groove 71 therein for engagement by eccentric pin 25 of shaft 22 through cylindrical cavity 38 of the cutting head. As the eccentric pin is rotated off-center by shaft 22, it induces back-and-forth lateral motion of blade holder 70 within slots 35 and 46 of the cutting head. This lateral motion results in the oscillation of blade 60. The superior portion of the cutting head includes offset region 39 adjacent a slot through which cutting blade 60 extends, providing clearance for the blade to oscillate through the corneal tissue, as shown in FIGS. 3B and 14B.

The superior and inferior portions of the cutting head are connected by lateral hinge 80, as shown in FIGS. 8 and 11. The hinge is composed of two solid pins 81, 82 that are commonly mounted to flat plate 83. The hinge pins are respectively mounted in the superior and inferior portions within cylindrical cavities 36 and 49, as shown in FIGS. 3B and 4. The hinge assembly maintains a constant connection between the superior and inferior portions, and permits the portions to be opened as shown in FIGS. 11 and 11A, for changing and cleaning blade 60 and/or float head 50. The closing together of cutting head portions 30 and 40 results in the engagement of transmission gears 33 and 47 required for moving the instrument across guide ring assembly 100. Threaded nut 90 screws about threaded cylindrical portions 31, 41 that are joined by the closing of the cutting head to couple superior and inferior portions 30, 40 together. Nut 90 further screws onto threaded cylindrical portion 23 of driving means 20, and thus provides a connective link between the driving means housing and the cutting head.

Figure 5B:
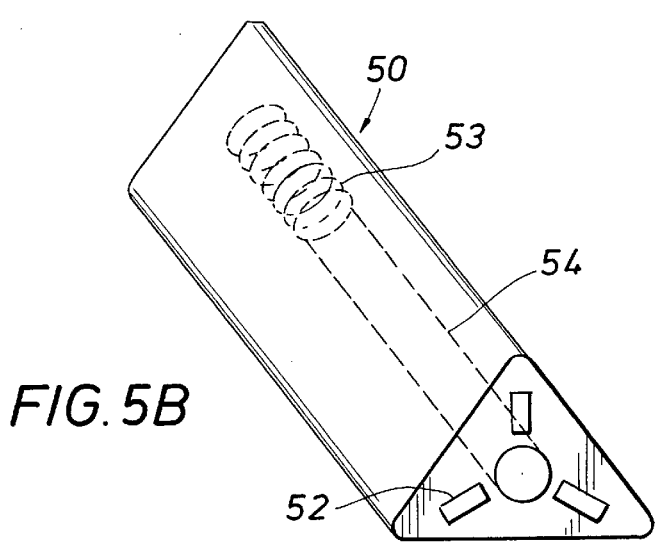
Figure 5C:
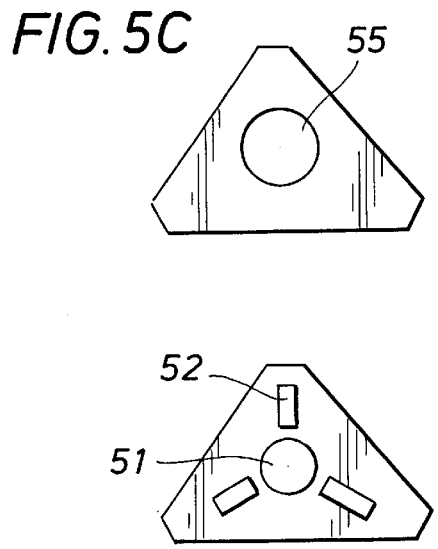
Figure 5D:
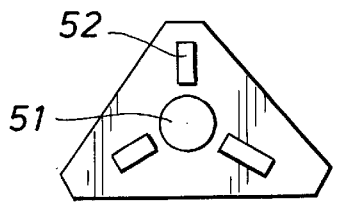

Adjustable float head assembly 50, shown in FIGS. 5–5D, is connected to the cutting head for at least partially compressing the cornea ahead of blade 60, so as to set the desired thickness of the corneal resection. Float member 50, also referred to as a "plaque," has a triangular cross-section and three selectable faces for compressing the cornea ahead of blade 60. Each face exhibits a relatively small surface area so as to minimize the portion of the cornea that is being compressed at any time during surgery.

Gliders 43, 44 of inferior portion 40 extend as parallel support arms, as seen in FIG. 4. The float is supported for rotation between triangular-shaped portions of the gliders, as shown in FIGS. 4A and 11D, about journal 54 that extends through the float and holes 48 in the gliders. Journal 54 is eccentrically mounted in bore 56 of float 50 so that each of the three faces are spaced at different distances from the journal. In this manner, the desired thickness of the corneal resection is varied by rotation of the float until the desired face is in position to compress the cornea. No disassembly of the microkeratome is necessary. The float head is further provided with indicia 57 for indicating the resection thickness provided by the selected face.

Glider 44 is equipped with grooves 42 for coupling and uncoupling float 50 from inferior cutting head portion 40. One end of float 50 is provided with raised bosses 52 which engage grooves 42 for locking the desired face of the float in the downwardly facing position to compress the cornea. The opposite end of the float is supported through coil spring 53 that allows for the disengagement of bosses 52 from grooves 42 by applying pressure to the float in the appropriate direction. Once the bosses are disengaged, the float can be rotated as desired and then released so that spring 53 will induce the bosses 52 to reengage with grooves 42. The faces of the float may be planar, arcuate, oblique, or any combination thereof, as shown in FIGS. 25, 25A, 25B, and 25C, respectively, whereby corneal lenticular resections can be performed by compressing the cornea with the appropriate face.

As seen in FIGS. 10 and 14B, microkeratome 10 further includes guide ring assembly 100 for placement on the eyeball, or ocular globe such that the globe's cornea 144 protrudes therethrough for the appropriate surgery. Guide ring 100 generally includes two circular sides, two straight parallel sides, and concentric opening 101 through which the cornea extends when the ring is affixed to the ocular globe.

Guide ring assembly 100 is composed of three elevational levels, as shown in FIG. 10C. Lower suction ring 107 is perforated and maintains the contact between the assembly and the eye through suction introduced via low pressure tube 106. In this manner, the eyeball is immobilized relative to the guide ring and the intraocular pressure is regulated. Intermediate ring 104 includes lateral gear track 103 for engagement by gear 47 of the cutting head, and defines the cutting path for the instrument across the cornea. Upper ring halves 102A, 102B are respectively equipped with 60° dovetail grooves 108, 109 that complement dovetail sections 43, 44 of inferior cutting head portion 40 to maintain smooth, continuous engagement between the instrument and the guide ring assembly. Those skilled in the art will appreciate that the guide ring assembly may be of various curvature ratios and diameters, as well as various heights, to allow for differences in eyeball sizes and to obtain corneal disks of varying diameters.

Stop means are also provided for limiting the range through which the blade is carried through the cutting path, in the form of stop riser 105 atop upper ring half 102B and adjustable screw 45 mounted to the inferior cutting head portion. Thus, FIGS. 14 and 14A illustrate the sequence of a typical corneal resection. In FIG. 14, the instrument is positioned atop the guide ring assembly for engagement therewith and screw 45 is separated from riser 105. In FIG. 14A, the instrument has been moved across plate 104 through the cutting path and screw 45 is in contact with riser 105, which has limited the motion of the instrument. In this manner, corneal hinges may be defined and created during incomplete lamellar keratotomies.

Magnifying lens, and pre-surgical corneal hinge meter 120 is illustrated in FIG. 12. This lens/meter is an independent component of the instrument, and allows for setting of the stop position using screw 45 by placing the meter under the guide ring assembly prior to attachment on the ocular globe. Reference marks 123, 124 are etched in the lens for precisely measuring the desired extent of corneal hinge according to the measured diameter of the cornea.

Setback, or return means are further provided for automatically reversing the driving means when the stop means limits the range of blade 60. FIG. 13 illustrates a preferred embodiment of the automatic setback circuit which is placed in the electric motor circuit that energizes the driving means described above. When screw 45 collides with riser 105, the voltage in the system will drop and cause the polarity of the current to be reversed. This reverses the rotation of driving means input shaft 21, and thereby causes the gear transmission system to reverse gear 47. In this manner, the microkeratome is returned to the position along the guide ring at which the surgery was initiated.

Figure 11B:
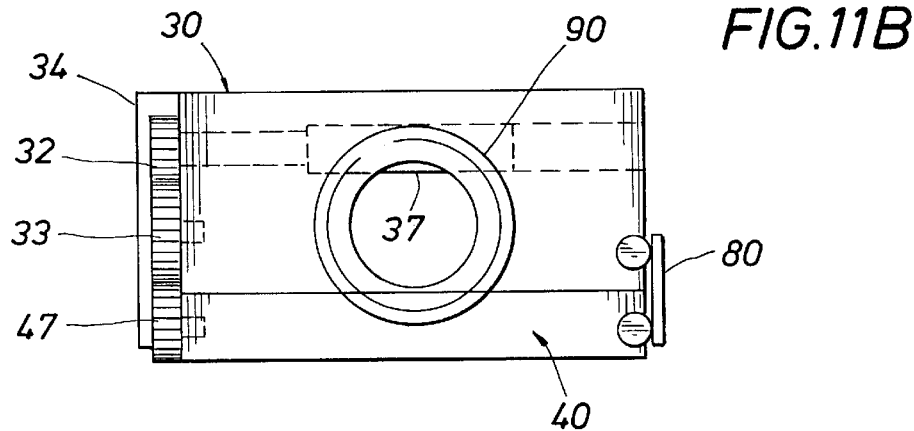
FIGS. 11B and 11C are rear and inferior projections, respectively, of the cutting head of FIG. 11 in a closed position.
Figure 11C:
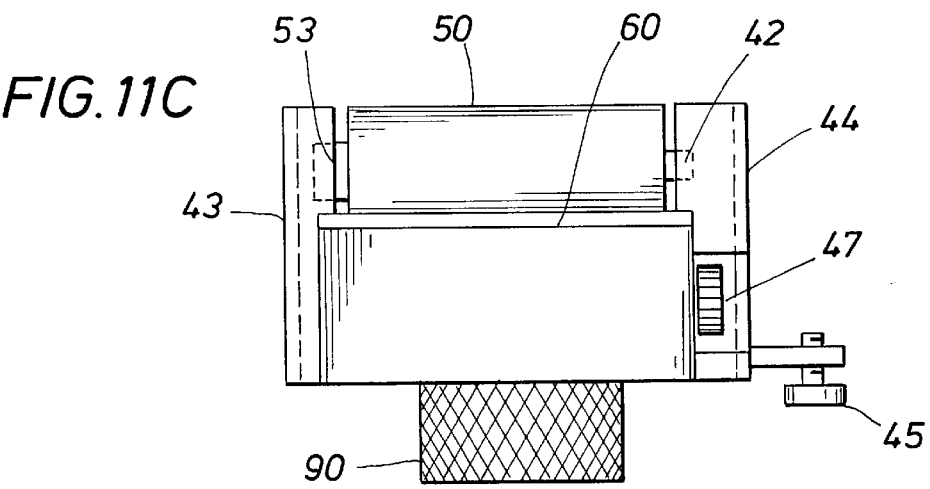
Figure 11D:
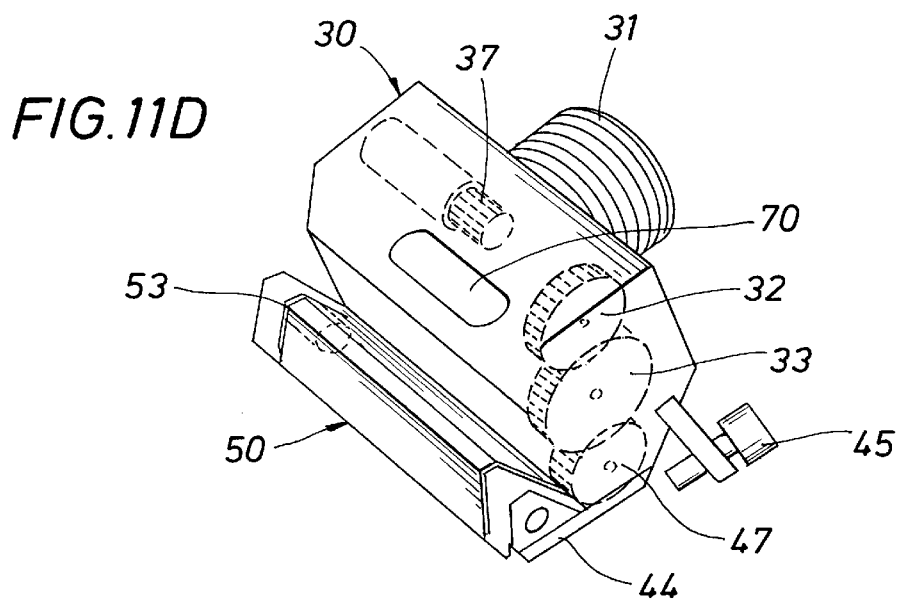
FIG. 11D is a transparent isometric projection of the assembled cutting head utilized in the embodiment of FIG. 1.
Figure 11E:
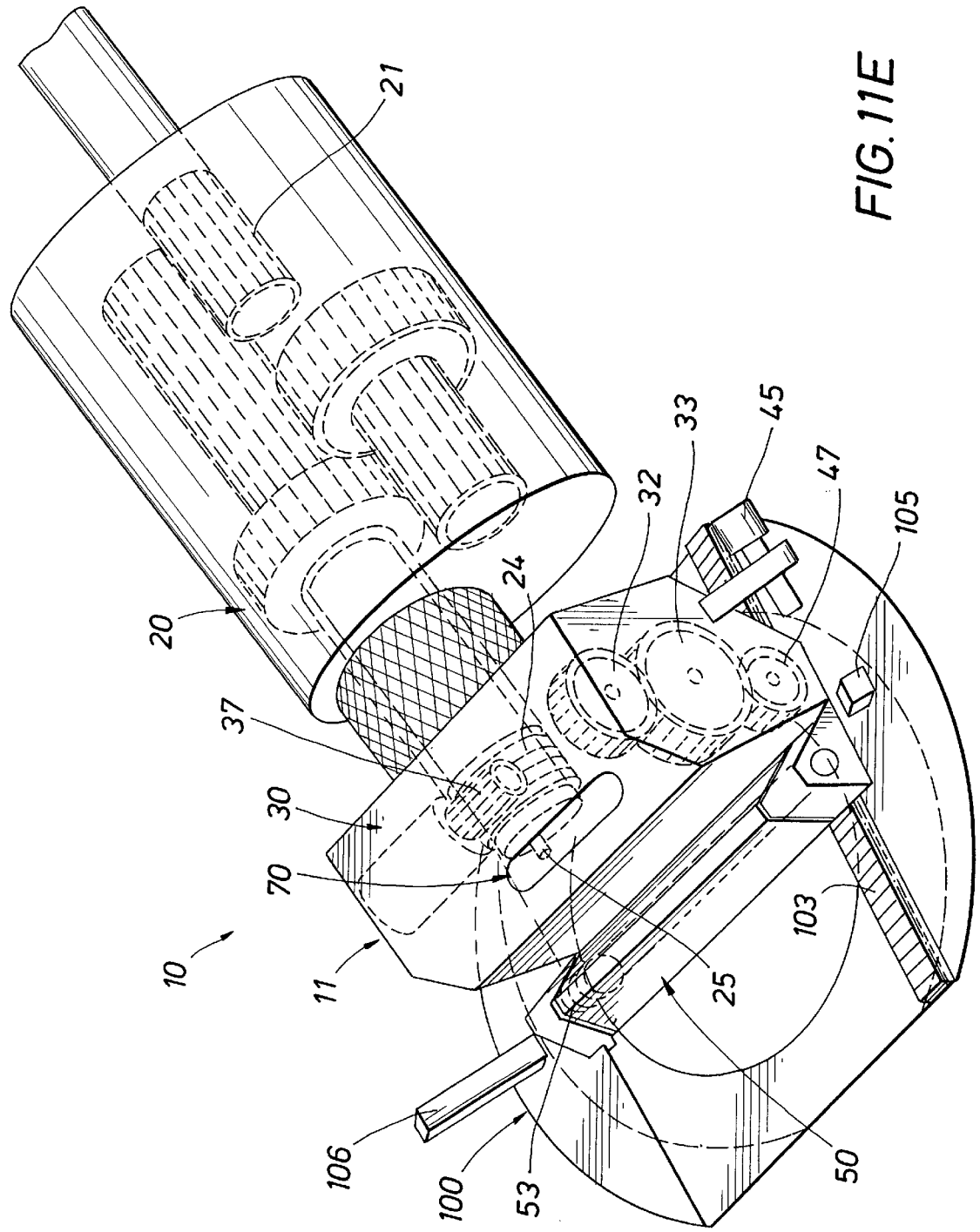
FIG. 11E is a transparent isometric projection of the microkeratome shown in FIG. 1.

The microkeratome is serviced between uses by opening the cutting head from its closed position as seen in FIGS. 11B and 11C. This requires that nut 90 be unscrewed from threaded portions 31, 41 at the rear part of the cutting head. Once the nut is removed, superior portion (30) can be flipped off of inferior portion (40) and set toward the lateral side as permitted by hinge 80, and as shown in FIGS. 11 and 11A. This system thus allows the opening of the cutting head up to 180°, facilitating the change and/or cleaning of blade 60 and float head 50.

Prior to every use of microkeratome 10, the desired depth of cut must be determined, and then set using the float head. To graduate the thickness of the resection, it is not necessary to remove float head 50 since the present invention allows it to be adjusted in place. In order to obtain the desired thickness of resection, the float head is pulled toward direction 111, as indicated in FIG. 11, and rotated in orientation 112 while looking for the appropriate indicia 57 marked on the float head. This allows for different thicknesses of cut, and avoids mistaken cut settings that could perforate the ocular globe. Furthermore, the float head has the important characteristic of performing only a partial flattening of the cornea, as shown in FIG. 14B. This is distinguishable from other microkeratomes that compress more than half and up to the entire cornea at any one time.

Once the desired face of float head 50 is selected, blade holder 70 is placed in cavity 35 of superior portion 30, as seen in FIG. 11, ensuring that the groove 71 is facing toward the rear part of the microkeratome to allow the entrance of eccentric pin 25 into the groove via threaded neck 31. Next, blade 60 is positioned so that its slot 61 fits onto head 72 of the blade holder.

At this point, microkeratome 10 is closed by flipping the superior cutting head portion back atop the inferior portion. The assembly of the cutting head portions causes the engagement of gear 33 with gear 47, as shown in FIG. 11D. The assembled portions are then coupled together by screwing nut 90 back onto joined threaded portions 31 and 41.

Having closed the cutting head with the forward threads of nut 90, the rear threads of nut 90 are threadably engaged with threaded portion 23 of driving means 20. This engagement positions eccentric pin 25 inside groove 71 of blade holder 70, and further causes the engagement of threaded portion 24 with worm gear 37 mounted for rotation in superior cutting head portion 30, as shown in FIG. 11E. The off-center rotation of eccentric pin 25 induced by the motor (not shown) inside vertical groove 71 of the blade holder generates an oscillatory movement of blade 60 that will permit the lamellar cut of the cornea.

The engagement of threaded shaft portion 24 to worm gear 37 within the superior cutting head portion of the microkeratome generates the well-known effect of a change of direction of the applied torque by 90°. Worm gear 37 is carried on a shaft that terminates at one end in gear 32. Gear 32 engages gear 33 of larger diameter, which in turn engages gear 47 in inferior portion 40 for transmitting a portion of the motor torque to guide ring assembly 100, and thereby moving the instrument through the cutting path. Thus, when the motor is activated, the cutting blade will oscillate at a high speed while gear 47 will be rotated at a relatively low speed.

Once the instrument is "armed" with the blade, the gliders 43, 44 of the inferior body are inserted inside the dovetails 108, 109 of the guide ring assembly, shown in FIG. 10C. This action causes gear 47 to engage gear track 103 for performing a uniform advance while the blade is oscillated transverse the cutting path.

The floor of the intermediate ring 104 has a shortened and rectangular surface area in the sense of the cut, and will permit the orientation of the instrument in any direction without colliding with the annexes of the eye. Thus, the present invention is capable of cutting in all directions because the apparatus has the capacity to cut without surpassing the borders of the guide ring assembly, as shown in FIGS. 14 and 14A.

After checking the operation of the microkeratome within the guide ring, magnifying lens and hinge meter 120 is placed beneath the inferior part of the ring in order to choose the desired diameter of resection, by adjusting screw 45 of inferior cutting head portion 40. Meter 120 is also useful when it is desired to create a corneal hinge for intrastromal surgery. In this event, the cutting blade is moved a predetermined distance substantially, but not completely across the portion of the cutting plane that intersects the cornea. The cutting blade is then moved back across the guide ring to its original position, so that the resulting corneal cap can be folded and secured over its hinge. At that point, the corneal stroma is resected as deemed appropriate, preferably by a laser. Meter 120 enables screw 45 to be adjusted according to the desired corneal hinge size.

Once screw 45 is set, surgical procedures are initiated by placing suction ring 107 on the ocular globe in the desired cutting direction. A vacuum pump (not shown) is activated to attract the cornea to concentric hole 101 of the suction ring at an appropriate pressure to maintain the cornea in a fixed position during the cut. At that time, gliders 43, 44 are re-introduced inside dovetails 108, 109 until gear 47 engages with gear track 103, as shown in FIG. 14.

Activation of the motor advances the instrument so as to first perform a partial flattening of the cornea and then cut the corneal disk until screw 45 collides with stop riser 105, as depicted in FIG. 14A. FIG. 14B illustrates the manner in which most of cornea 144 remains uncompressed by the float head while the cut is performed. The collision produces a voltage drop, triggering a reverse of the current polarity in the motor circuit, and the return of the microkeratome to its place of origin on the guide ring assembly. Those skilled in the art will appreciate that superior lid 141 of the eye doesn't interfere with the travel of the apparatus.

Pivoting Embodiments of the Microkeratome

The present invention further contemplates additional embodiments of the microkeratome, referred to generally as 210, which are the presently preferred embodiments, as are shown in FIGS. 15–24. Thus, with reference to FIGS. 15, 17, and 18, guide ring 200 may be equipped with upwardly extending pivot post 203 that is engageable with output shaft 242 partially disposed within cutting head 230. Output shaft 242 is positioned in engagement with the gear assembly that cooperates with the driving means such that a torque is applied to the output shaft by a drive motor connected to driving means 20 of the microkeratome. Thus, the output shaft, if unconstrained, will rotate.

However, the engagement of output shaft 242 with pivot post 203, which is fixed to guide ring 200, prevents the output shaft from rotating when the guide ring is affixed to the patient's eye. Thus, the torque applied to output shaft 242 will induce the microkeratome to be rotated about the output shaft, as explained further below. Pivot post 203 is further designed to support the weight of the microkeratome via guide tube 236 about the output shaft, at support ring 209. In this fashion, the cutting head is driven across guide ring 200, by the action of drive gears against a worm gear on the fixed output shaft, through an arcuate path in a smooth, controlled fashion.

This is contrasted with the previously described embodiment, as well as other prior art microkeratomes, wherein the microkeratome is driven across the guide ring by the engagement of a drive gear with a gear track positioned on the surface of the guide ring. The arcuate sweeping motion of the cutting head of microkeratome 210 is believed to provide a much smoother surgical stroke since variables resulting from the surgeon's input are eliminated. Once output shaft 242 and pivot post 203 are placed in engagement, the gear assemblies and associated bearings within cutting head 230 along with the electric motor and driving means 20 control the motion of the microkeratome. Thus, the smooth motion of the instrument is largely dependent on the precise manufacturing tolerances for the gear assemblies and the support structure provided by the pivot post at the output shaft, rather than the expertise of the surgeon.

With reference again to FIG. 2A, driving means 20 includes a speed reduction system and an eccentric pin assembled in a single unit. Thus, a drive motor (not shown) produces a torque in shaft 21, which rotates central shaft 22 that terminates in small eccentric pin 25 and worm gear 24. Eccentric pin 25 drives cutting blade 60 in similar fashion to that described above. Worm gear 24 ultimately drives the microkeratome across the guide ring about pivot post 203, as explained further below.

Driving unit 20 also includes externally threaded neck portion 23 which permits it to engage complementary internally threaded neck portion 231 on cutting head 230, as shown in FIG. 17. Threaded cylindrical portion 231 extends outwardly from hollow cavity 239, which houses blade holder 270. Cavity 239 exhibits a greater width than blade holder 270 so as to permit reciprocating movement of the blade holder in a horizontal plane, as described above with regard to microkeratome 10.

Cutting head 230 also contains cylindrical cavities that house first and second worm shafts 241 and 242. The first and second worm shafts are mounted for rotation about their respective axes, positioned 90° relative to one another as shown in FIGS. 17 and 18. Worm gear 24 of central shaft 22 of driving means 20 engages reduced diameter gear portion 232 of first worm 241 to transmit torque from central shaft 22 to first worm 241. Worm 241 is further equipped with worm gear 233 adjacent one of its ends, and is mounted for rotation about its axis. Worm gear 233 of first worm 241 engages reduced diameter gear portion 244 of second worm 242, which is also referred to as the output shaft. In this fashion, torque delivered from central shaft 22 is transmitted through worm shaft 241 to output shaft 242, which is mounted for rotation about an axis that is oriented 900 to the axis of first worm 241.

Cutting head output shaft 242 terminates in a gear toothed coupling system 235 that engages an opposing gear toothed coupling system 204 of pivot post 203. As mentioned above, output shaft 242 and coupling teeth 235 would rotate freely upon activation of the drive motor prior to engagement with coupling teeth 204 of post 203. However, the engagement of the opposing coupling teeth fix output shaft 242 to guide ring 200, preventing the output shaft from rotating relative to the guide ring. Thus, the torque applied by first worm 241 to output shaft 242 results in a back-drive rotation of worm 241 about output shaft 242. In other words, the rotation of worm 241 about its axis and the engagement of worm gear 233 with reduced diameter gear portion 244 of output shaft 242 induces worm 241 to rotate in a horizontal plane about the axis of output shaft 242. Since worm 241 is carried for rotation about its axis within cutting head 230, the entire cutting head is also rotated in the horizontal plane about the axis of output shaft 242 and pivot post 203 to perform the desired cutting action.

In addition to cavity 239, cutting head 230 is provided with cavity 239A accessible through a lateral slot inclined at an angle between 26° and 30° along plane 239B, as shown in FIG. 17A. The inclined lateral slot permits the insertion or ingress of head 272 of blade holder 270, which are also illustrated in FIGS. 20–20B. Cavity 239 thus houses blade holder 270, while cavity 239a contains blade 60, shown in FIG. 6, which is mounted to head 272 via blade opening 61 in similar fashion to that described above for microkeratome 10. In this manner, blade holder 270 and blade 60 are free to move horizontally by the rotation of eccentric pin 25 within vertical slot 271 of blade holder 270.

The front, lower portion of cutting head 230 carries float head 250, also referred to as a plaque, for compressing the cornea ahead of the cutting blade so as to provide a desired depth of cut and thickness of the resulting corneal flap. Float head 250 is mounted between lower vertical support arms positioned on either side of the float head, about shaft 254 which is carried for rotation within openings 239C in the support arms. The openings thus support the shaft for the rotation of float head 250.

Figure 15:
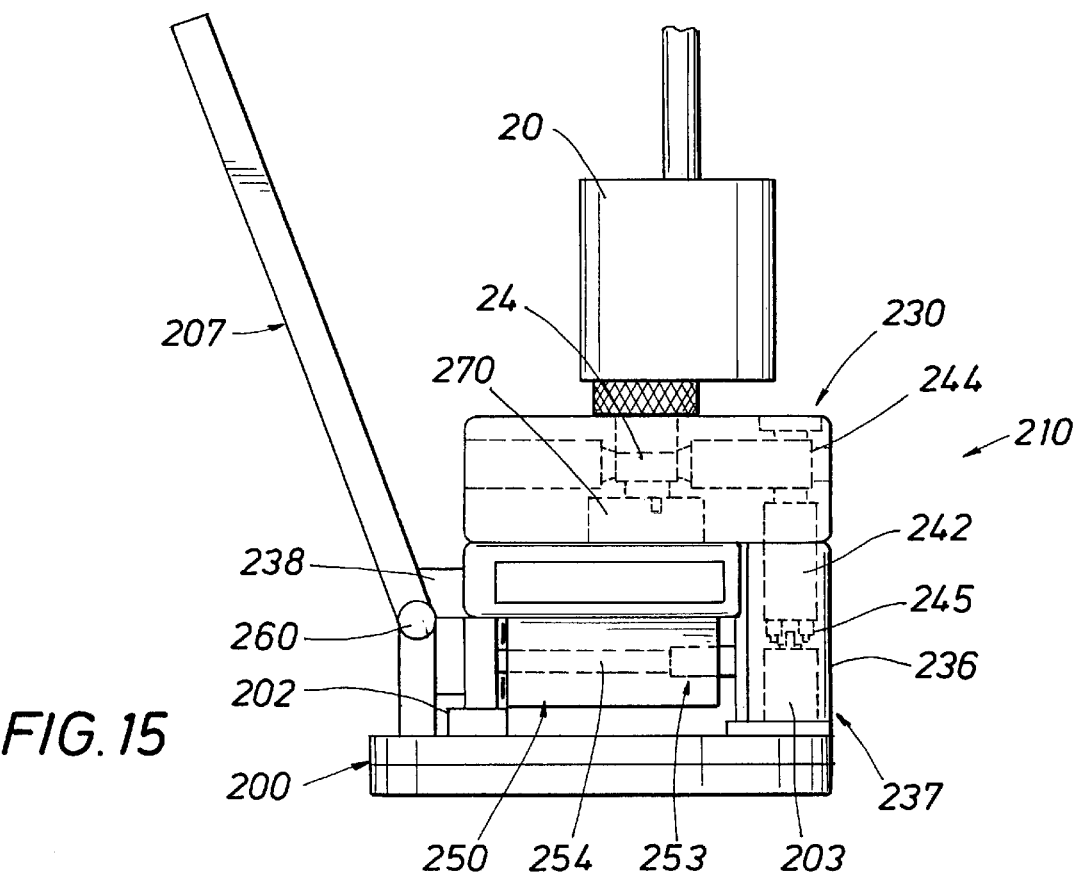
FIG. 15 is a frontal projection, partially transparent, of a microkeratome and guide ring assembly in accordance with a preferred embodiment of the present invention.
Figure 16:
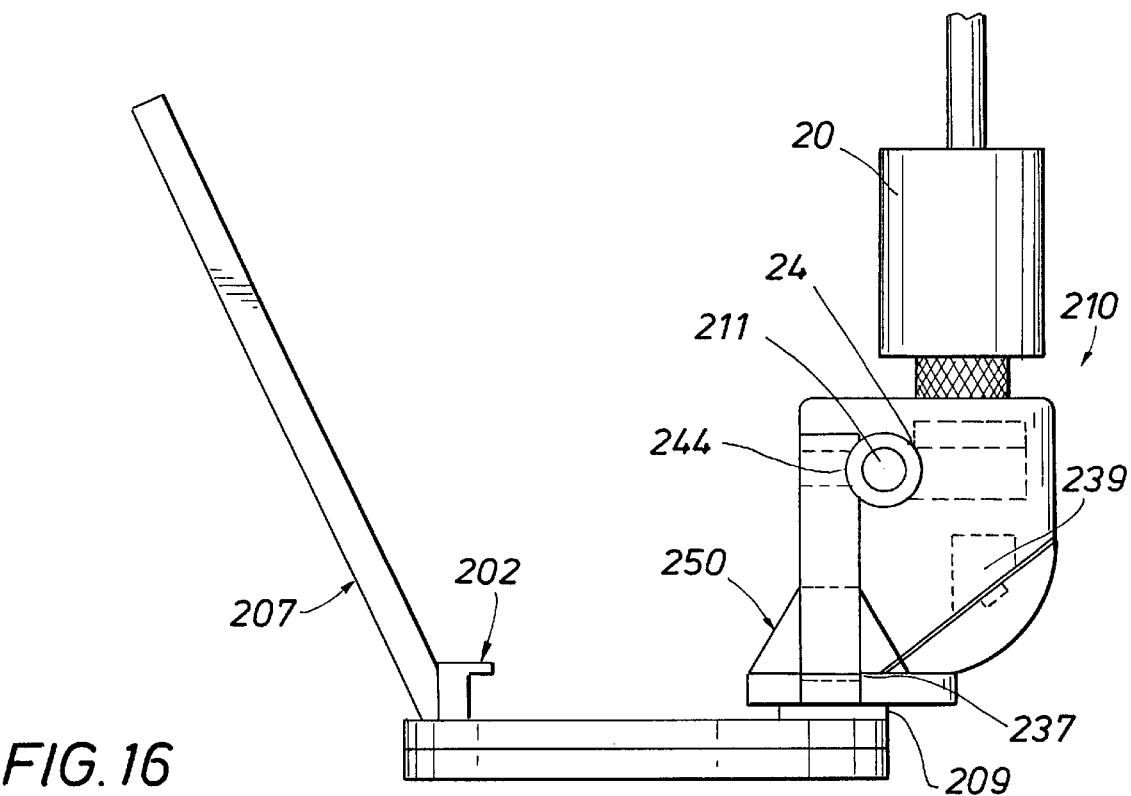
FIG. 16 is a lateral projection of the microkeratome of FIG. 15, with the microkeratome shown in the starting position for performing a corneal incision.

As with the float head described above for microkeratome 10, float head 250 of microkeratome 210 is relatively short in length and exhibits a triangular shape with a central eccentric bore 251 through which rotation about shaft 254 is accomplished, as shown in FIG. 15 and 17. Eccentric bore 251 permits the selection of different cutting heights with respect to the edge of the blade, and as a result different thicknesses for the resulting corneal flap. Shaft 254 is provided with raised boss members or positioning members on one of its ends that permit it to be selectively positioned within the support arms. Thus, one of the float head support arms is equipped with slots 239D for engagement with the positioning members 252 of the float head. Spring 253 is positioned in the opening in the other float head support arm about shaft 254, to permit positioning members 252 to be yieldably displaced from slots 239D to make the desired selection among the three faces of the float head. In this manner, float head 250 is easily rotated to a desired cutting depth and then locked in place by allowing spring 253 to urge positioning members 252 back into engagement with slots 239D.

The figures further show microkeratome 210 equipped with an optional guide assembly for ensuring that the cutting head does not uncouple from guide ring 200. Thus, cutting head 230 may be provided with guide wheel 239E that is mounted for rotation to one of the float head support arms, as shown in FIG. 17. Shoulder member 202 affixed to guide ring 200 serves as a guide for the passage of wheel 239E and prevents the uncoupling of the cutting head with the guide ring during the corneal incision. This guide assembly is thus secondary to the guide provided by the engagement of pin 237 with circular groove 206, as explained further below.

The engagement between the pivot post and the output shaft is illustrated in the drawings, particularly FIGS. 18–18C, as being accomplished through alternative structures. Thus, the pivot post may be tubular and have an opening through the top thereof that is adapted for engagement with splines 242a positioned along the length of the output shaft as illustrated in FIG. 18C. In this embodiment, the splined shaft includes a guide tube (not shown) similar to guide tube 236 of the preferred embodiment, having an inner diameter that is greater than the outer diameter of the tubular pivot post. The guide tube includes an internal pin 237 that aligns splines 242a of the output shaft properly within pivot post 203a when the pin is positioned within groove 205a formed on the outer surface of the pivot post. Pin 237 of the guide tube further ensures that the instrument remains coupled to guide ring 200 by engaging circular groove 206a as the cutting head is driven about an arcuate path over the guide ring.

As described above, in the preferred embodiment of microkeratome 210, pivot post 203 and output shaft 242 are equipped with opposing coupling teeth that are adapted for engagement with one another. The output shaft is provided within guide tube 236 that is equipped with pin 237 for properly aligning teeth 235 of the output shaft with teeth 204 of the pivot post when the pin is placed within groove 205 in the pivot post. Pin 237 further engages circular groove 206 at the bottom of post 203 to ensure that cutting head 230 remains coupled to guide ring 200 during the cutting motion of the instrument across the guide ring. Those skilled in the art will realize that other structures that rigidly constrain the output shaft from rotating relative to the pivot post will be equally suitable for purposes of the present invention.

Figure 24:
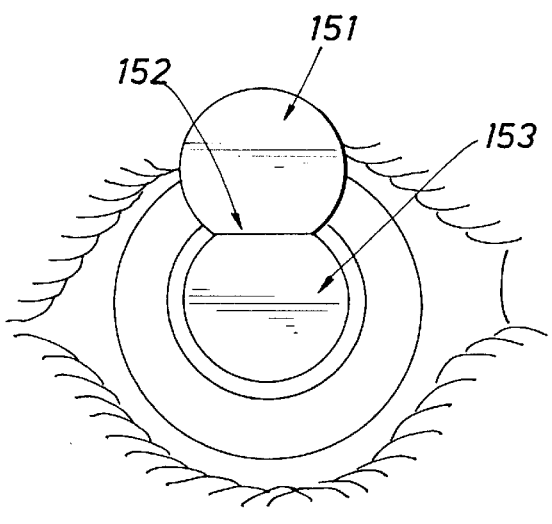
FIG. 24 is a superior projection of the patient's eye illustrating a corneal flap hinged at the superior region of the cornea, in accordance with the use of the present invention.

The present invention is thus well suited for making corneal incisions in any direction. Of particular importance is the fact that the present invention is capable of making incisions from the inferior portion to the superior portion (i.e., lower to upper) of the cornea to create corneal flap 151 and hinge 152 in the superior (upper) quadrant of the eye, as shown in FIG. 24. Studies have shown that such superior hinges are much less likely to experience ablation and traumatic displacement following surgery than a conventional nasal hinge. Thus, a nasal hinge cannot prevent movement of the corneal flap under the vertical reciprocating motion of the eyelid. A superior or upper hinge, on the other hand, will keep the corneal flap in place under blinking action of the eyelid.

The extent of the corneal incision is controlled by adjustable stop means 260, similar to that described in the previous embodiment, that limits the sweeping motion of cutting head 230 across guide ring 200 to provide the appropriate extent of corneal hinge. The stop means are adjusted by merely turning the screw that extends through arm 207 to vary the point at which stop member 238 of cutting head 230 contacts screw 260. As described previously, when the stop member is contacted, the control circuit shown schematically in FIG. 13 automatically returns the instrument to its starting position.

The operation of the pivoting embodiment of the microkeratome will now be summarized. First, the desired thickness of the corneal flap or disc to be created must be determined. In many cases, it will not be necessary to remove float head 250 from the instrument, since the float head is provided with three faces for creating three distinct depths of corneal incision.

Again, to achieve the desired resection thickness, the float head is pulled toward the support arm carrying spring 253 and is rotated to seek the desired thickness as indicated by indicia that is pre-marked on the float head or plaque. Thus, different thicknesses of corneal cut are readily obtainable and errors due to improper cutting depth are avoided. The adjustable float head of the present invention has the important characteristic of inducing only a partial flattening of the cornea (less than 8 millimeters) at the time that the cut is carried out, which is different from other known microkeratomes that flatten more than half of the entire section of the cornea. Those skilled in the art will appreciate that this characteristic results primarily from the small surface area exhibited by any one face of the float head. Thus, float head 250 could provide superior results independently of its adjustable feature.

Next, a sterilized blade 60 is assembled in blade holder 270 through the slot that extends between cavities 239 and 239A of the cutting head, by introducing head 272 of the blade holder into blade opening 261. Blade 60 is thereby mounted in the blade holder with the sharp edge of the blade is oriented in a downward direction following the angle of the line 239B, seen in FIG. 17A. At this time, slot 271 of the blade holder is positioned toward the upper part of the cutting head 230, to later permit the entry of the eccentric pin 25 on driving means 20.

Next, the drive motor is coupled to the microkeratome by threadably engaging neck 231 of the cutting head to neck 23 of driving means 20 connected to the motor. This engagement introduces eccentric pin 25 into slot 271 of blade holder 270, and further positions worm gear 24 in engagement with reduced diameter gear portion 232 of first worm 241. With these connections in place, operation of the drive motor will induce horizontal reciprocal motion of blade holder 270 and blade 260 within the cutting head while simultaneously inducing rotation of output shaft 242 before it is coupled to pivot post 203. Also, because of the particular gear arrangements, when the drive motor is activated, the blade shall be moved at a relatively high speed while the output shaft is rotated at a relatively low speed.

After verifying that the driving means including the motor are properly coupled to the cutting head, the assembly is temporarily set aside so that the extent of the corneal hinge may be regulated. As previously described with reference to FIGS. 12–12B, hinge regulating tool 120 is set in place atop the cornea in cooperation with guide ring 200 to measure and mark the size of the corneal hinge beneath the ring. The tool 120 is transparent and permits the surgeon to see the desired advance of the cutting blade magnified when it is placed under the ring, and to regulate the desired stop in accordance with the desired diameter of the resulting corneal disc, using marked diameters 123, 124 on the lower face of the lens 121 as a reference. Lens 120 is thus set in place to map the limit of travel by the microkeratome over guide ring 200 and to choose the desired diameter for the corneal disc, which variables are obtained by regulating stop means 260 and float head 250.

Once the desired size and extent of corneal cut is set, guide ring 200 is affixed to the cornea by applying suction from a low pressure source through a cavity in arm 207 connected to the guide ring such that cornea 141 protrudes therethrough at an adequate pressure to maintain the ocular globe in a fixed position during the intended surgery. In this manner, the eyeball is immobilized relative to the guide ring and the intraocular pressure is regulated.

The microkeratome is then placed on guide ring 200, as shown in FIGS. 15 and 18–18C. Tubular guide 236 of the microkeratome 36 is placed over pivot post 203 while pin 237 is oriented to align first with linear groove 205 and then with groove circular 206 which communicates with groove 205.

Figure 21:
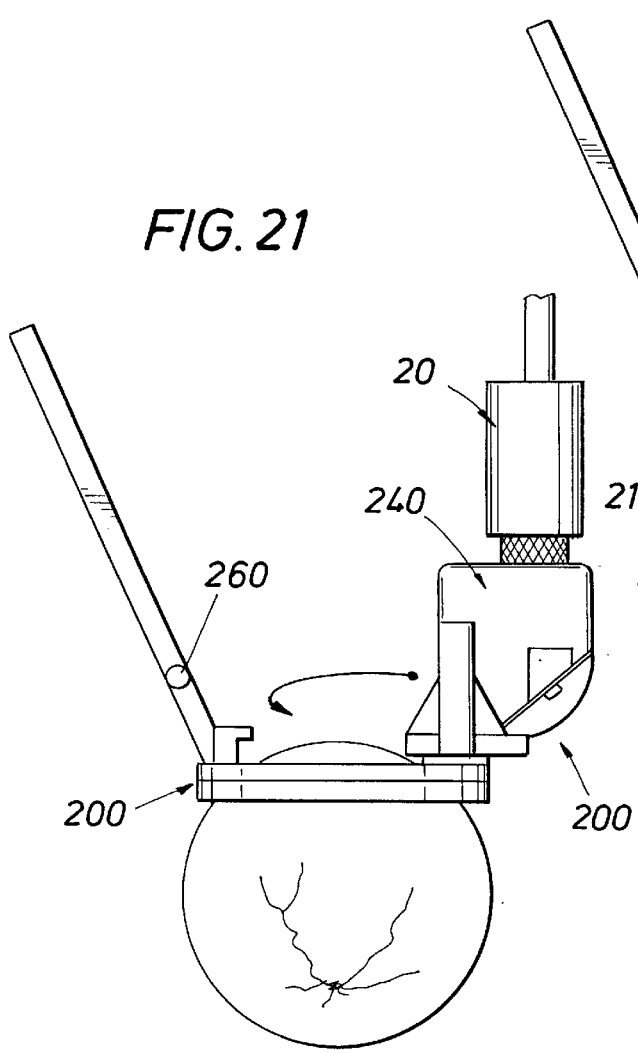
FIGS. 21 and 22 illustrate the starting and stopping positions of the preferred microkeratome during the performance of a corneal resection.
Figure 22:
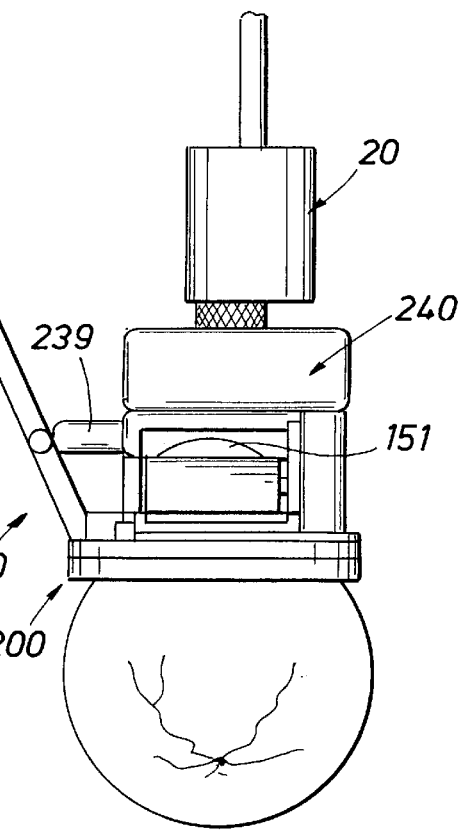
Figure 23:
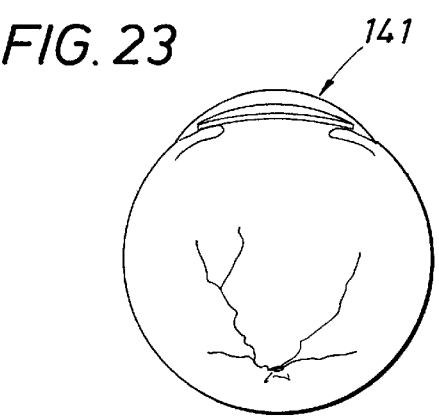
FIG. 23 is a lateral projection of a patient's eye prior to the corneal incision.

With the cutting head coupled to the guide ring, the drive motor is activated to initiate the corneal incision, as indicated in FIG. 21. Upon activation, the microkeratome advances in an arcuate path as worm gear 244 rotates cutting head 230 about output shaft 242 at reduced diameter gear portion 233. Float head 250 produces a partial flattening of cornea 141 while the cutting blade performs the incision. This cutting action is continued across the arcuate path until stop member 238 encounters screw 260, defining corneal flap 151 and hinge 152 as shown in FIGS. 22 and 24. When this occurs, a voltage drop is produced in the system and the polarity of the current is reversed, returning the microkeratome to its point of origin.

Those skilled in the art will appreciate that the relatively small surface area exhibited by the pivoting microkeratome of the present invention gives the instrument the capacity of operating without passing over the edges of the guide ring. This permits the cutting head to be placed in its initial position and to be driven at the pivot post for cutting action in a sweeping arcuate path without stumbling over or interfering with the edges of the eye. More importantly, this permits the creation of a corneal hinge in the upper or superior quadrant. Thus, corneal disc or flap 151 which results from the action of the microkeratome is raised posteriorly such that hinge 152 remains in the superior quadrant. This of course permits the shaping of corneal stroma tissue 153, currently carried out with laser technology.

Concave, Convex, and Oblique Corneal Plaques

Figure 26:
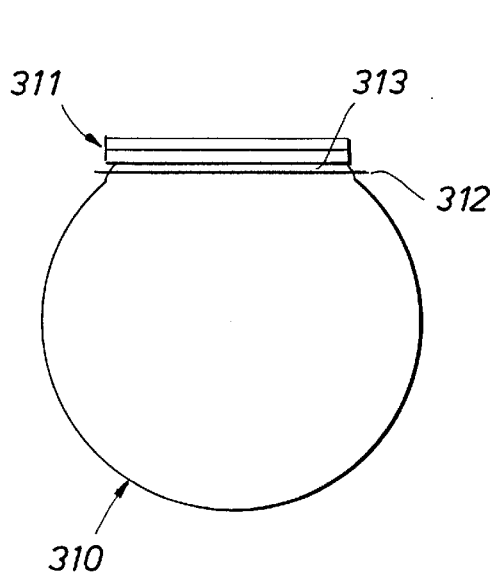
FIG. 26 is a frontal projection of the cut of an eye with a flat plaque, and its relationship with the blade.
Figure 26A:
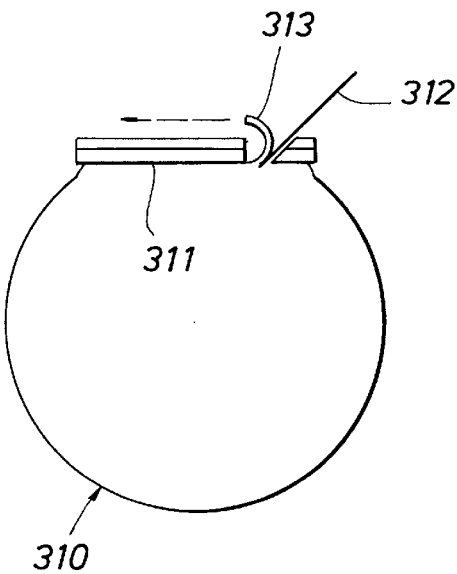
FIG. 26A is a lateral projection with a blade at an angle of attack.
Figure 26B:
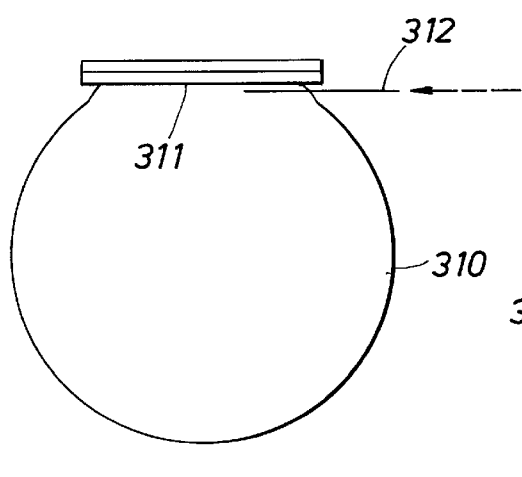
FIG. 26B is a lateral projection without any angle of attack by the blade.

The present invention further contemplates the use of various plaques, or float heads, to perform lamellar keratotomies of non-parallel faces (lenticula) with the purpose of supplementing the current techniques of idrefractive surgery in which only keratotomies or keratectomies of parallel faces (disks) are obtained. Thus, FIG. 26 shows the surface of flat plaque 311 and its relationship with blade 312 in which the tissue located between them, i.e., tissue 313 to be cut, remains of the same thickness in both meridians, as explained further below. FIG. 26A illustrates a lateral view in which blade 312 is observed with an angle of attack that requires the plaque to be displaced with the blade to perform the cut. FIG. 26B shows the same lateral view, but with a blade without an angle of attack, which allows the plaque to remain stationary while the blade performs the cut.

Figure 26C:
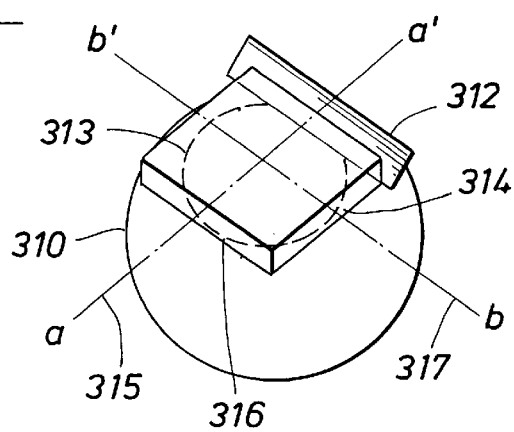
FIG. 26C is a superior transparent isometric projection of a plaque on the eye, and the plane of the blade.

FIG. 26C is an isometric view of a transparent plaque, and its relationship with blade 312 and with eye 310. The corneal surface for refractive effects is described with regard to its two main meridians that are the horizontal and the vertical. For purposes of explanation of the different corneal cuts, the two main meridians will be the one a–a' that continues the direction of the cut of the apparatus 315, and the one b–b' that crosses 90°, 317. The surface of the plaque that enters in contact with cornea 316 and 314 will be described according to these meridians.

Figure 27:
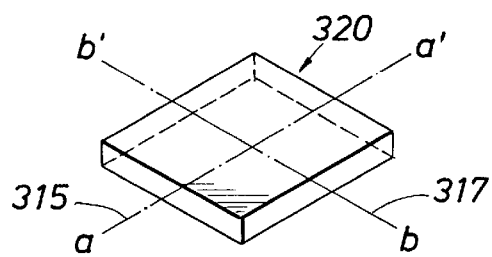
FIG. 27 is an isometric projection of a flat plaque and its two main meridians.
Figure 27A:
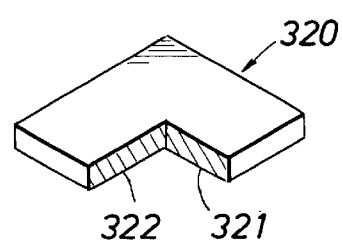
FIG. 27A is an isometric projection of the plaque with a longitudinal and cross-sectional partial cut.
Figure 27B:
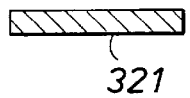
FIG. 27B is a cross-sectional cut of the meridian a–a'.
Figure 27C:
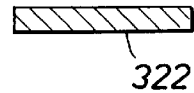
FIG. 27C is a cross-sectional cut of the meridian b–b'.

FIG. 27 illustrates a plaque of flat surface 320 in both meridians that is used for virtually all the prior microkeratomes. FIG. 27A is a partial longitudinal and cross-sectional cut of the plaque that shows the form of the surface in its two main meridians. FIG. 27B is a cross-sectional cut of the meridian a–a', and FIG. 27C is a cross-sectional cut of the meridian b–b', which in both cases are flat.

Figure 28:
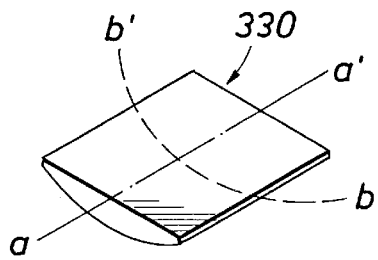
FIG. 28 is an isometric projection of a flat-convex plaque and its two main meridians.
Figure 28A:
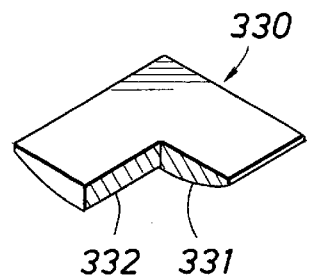
FIG. 28A is a longitudinal and cross-sectional partial cut for better visualization.
Figure 28B:
FIG. 28B is a cross-sectional cut of the meridian a–a'.
Figure 28C:
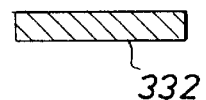
FIG. 28C is a cross-sectional cut of the meridian b–b'.

FIG. 28 shows a flat-convex plaque 330, i.e., a plaque of convex surface in meridian a–a', and of flat surface in the other meridian b–b' that allows for negative lenticula (thicker in the periphery) in one meridian and flat in the other. FIG. 28A is a partial longitudinal and cross-sectional cut of the plaque that shows the form of the surface in its two main meridians 331 and 332. FIG. 28B is a cross-sectional cut of meridian a–a' of the plaque that is convex, and FIG. 28C is a cross-sectional cut of the meridian b–b' that is flat. This flat-convex plaque is usable in the microkeratomes having moving plaques, such as float head 50 described above, and in those of stationary plaques.

FIG. 29 shows flat-concave plaque 340, i.e., a plaque of concave surface in a meridian a–a', and of flat surface in the other meridian b–b'. Plaque 340 obtains positive lenticula in one meridian (thicker in the center) and flat in the other. FIG. 29A shows a partial longitudinal and cross-sectional cut of the plaque that shows the form of the surface in its two main meridians 341 and 342. FIG. 29B is a cross-sectional cut of meridian a–a' of the plaque that is concave, and FIG. 29C is the cross-sectional cut of meridian b–b' that is planar. This flat-concave plaque allows for astigmatic positive lenticula in one meridian and flat in the other. This type of plaque could also be used in the microkeratomes having moving plaques and in those of stationary plaques.

FIG. 30 shows a biconvex plaque 350, i.e., a plaque of convex surface in both meridians (a–a' and b–b'). It provides negative lenticula in both meridians (thicker in the center). FIG. 30A is a partial longitudinal and cross-sectional cut of the plaque that shows the form of the surface in its two main meridians 351 and 352. FIG. 30B is a cross-sectional cut of the meridian a–a' of the plaque that is convex. FIG. 30C illustrates that the cross-sectional cut of the meridian b–b' is also convex. This biconvex plaque provides negative lenticula in both meridians when it is used with microkeratomes having stationary plaques only. In those instruments having moving plaques, it will cut astigmatic negative lenticula.

FIG. 31 shows a biconcave plaque 360, i.e., a plaque of concave surface in both meridians (a–a' and b–b') that provides positive lenticula in both meridians (thicker in the center). FIG. 31A is a partial longitudinal and cross-sectional cut of a plaque that shows the form of the surface in its two main meridians 361 and 362. FIG. 31B is a cross-sectional cut of meridian a–a' of the plaque that is concave. FIG. 31C shows that the cross-sectional cut of the meridian b–b' is also concave. This biconcave plaque provides positive lenticula in both meridians when it is used with microkeratomes of stationary plaques. In those instruments with moving plaques, it will cut astigmatic positive lenticula.

Figure 32:
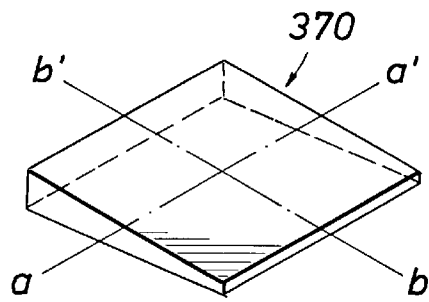
FIG. 32 is an isometric projection of an oblique plaque and its two main meridians.
Figure 32A:
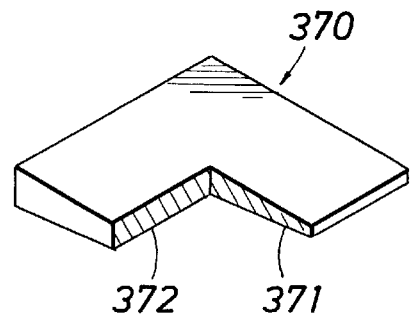
FIG. 32A is an isometric projection of the oblique plaque with a longitudinal and cross-sectional partial cut.
Figure 32B:
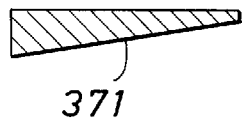
FIG. 32B is a cross-sectional cut of the meridian a–a'.
Figure 32C:
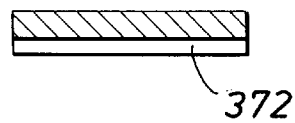
FIG. 32C is a cross-sectional cut of the meridian b–b'.

FIG. 32 shows an flat-oblique plaque 370, i.e., a plaque of oblique surface in meridian a–a', and of flat surface in the other meridian b–b' that allows for oblique lenticula (thicker on one side) in one meridian and flat in the other. FIG. 32A is a partial longitudinal and cross-sectional cut of the plaque that shows the form of the surface in its two main meridians 371 and 372. FIG. 32B is a cross-sectional cut of meridian a–a' of the plaque that is oblique, and FIG. 32C is a cross-sectional cut of the meridian b–b' that is flat. This flat-oblique plaque is usable in the microkeratomes having moving plaques, such as float head 50, and in those of stationary plaques.

Figure 33:
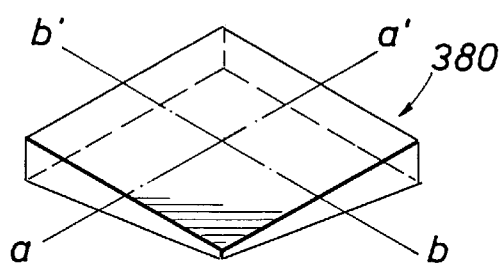
FIG. 33 is an isometric projection of a bi-oblique plaque and its two main meridians.
Figure 33A:
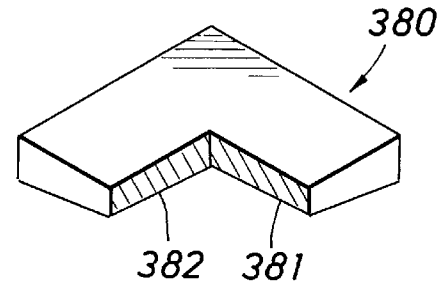
FIG. 33A is an isometric projection of the bi-oblique plaque with a longitudinal and cross-sectional partial cut.
Figure 33B:
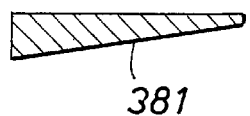
FIG. 33B is a cross-sectional cut of the meridian a–a'.
Figure 33C:
FIG. 33C is a cross-sectional cut of the meridian b–b'.

FIG. 33 shows a bi-oblique plaque 380, i.e., a plaque of oblique surface in both meridians (a–a' and b–b') that provides oblique lenticula in both meridians (thicker on one side). FIG. 33A is a partial longitudinal and cross-sectional cut of a plaque that shows the form of the surface in its two main meridians 381 and 382. FIG. 33B is a cross-sectional cut of the meridian a–a' of the plaque that is oblique, and FIG. 33C shows the cross-sectional cut of meridian b–b' also being oblique. This bi-oblique plaque provides oblique lenticula in both meridians when it is used with microkeratomes of stationary plaques. In those instruments with moving plaques, it will cut astigmatic oblique lenticula.

Figure 25:
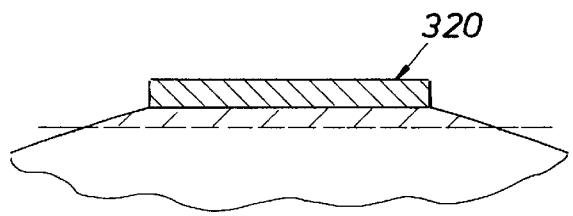
FIGS. 25, 25A, 25B, and 25C are frontal projections of planar, concave, convex, and oblique float heads, or plaques, for compressing the cornea to specific shapes.
Figure 25A:
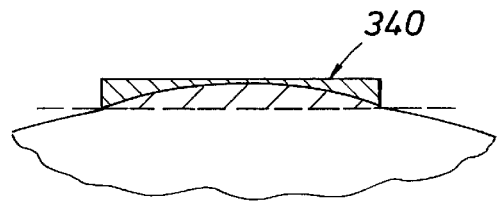
Figure 25B:
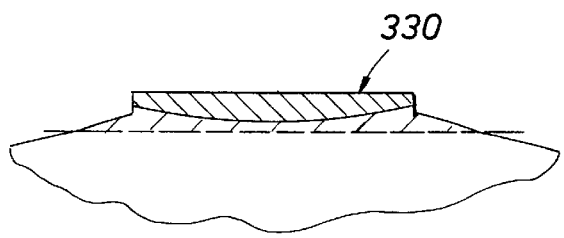
Figure 25C:
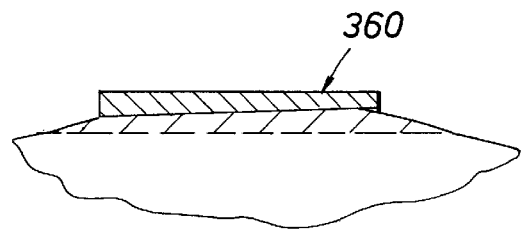

Referring back to FIG. 25, a cross-sectional cut of flat plaque 320 is shown with the tissue between the plaque and the blade having parallel faces. FIG. 25A shows a cross-sectional cut of concave plaque 340 with the tissue between the plaque and the blade having a positive upper surface. FIG. 25B shows a cross-sectional cut of convex plaque 330 with the tissue between the plaque and the blade having negative upper surface. FIG. 25C shows a cross-sectional cut of oblique plaque 360 wherein the tissue between the plaque and the blade has an oblique upper surface.

In summary, these plaques can be used in the microkeratomes having stationary plaques as well as in those having moving plaques. The microkeratomes of stationary plaque will obtain positive or negative lenticula in both spherical or astigmatic cases if they use concave, convex, or oblique plaques. This is contrasted with those of moving plaque, that provide the positive, negative, or oblique power of a lenticula in a single meridian, since the other meridian will always be flat.

From the foregoing it will be seen that this invention is one well adapted to attain all of the ends and objects hereinabove set forth, together with other advantages which are obvious and which are inherent to the method and apparatus.

It will be understood that certain features and subcombinations are of utility and may be employed without reference to other features and subcombinations. This is contemplated by and is within the scope of the claimed invention.

Because many possible embodiments may be made of the invention without departing from the scope thereof, it is to be understood that all matter herein set forth or shown in the accompanying drawings is to be interpreted as illustrative and not in a limiting sense. For example, in certain instances it may be desirable to resect asymmetric corneal lenticula for refractive correction.

What is claimed is:

1. A microkeratome for performing a lamellar keratotomy of an ocular globe, comprising:
   a guide ring for placement on the ocular globe such that the globe's cornea protrudes therethrough, said guide ring includes an upwardly extending pivot post;
   means for temporarily fixing said guide ring to the ocular globe;
   a blade suitable for corneal resections;
   a cutting head for carrying said blade over said guide ring through a cutting path defined by said guide ring;
   an adjustable cornea compression device connected to said cutting head for at least partially compressing the cornea ahead of said blade so as to set the corneal resection to a desired shape and thickness;
   means for driving said cutting head and said cornea compression device across said guide ring, whereby said blade cuts at least partially through the cornea to perform the lamellar keratotomy, said driving means including an output shaft that extends downwardly through said cutting head for engagement with the pivot post to constrain the output shaft against rotation relative to the pivot post, and means for applying a torque to the output shaft within said cutting head, whereby said cutting head and said cornea compression device are rotated about the output shaft by said driving means over said guide ring at a controlled speed.

2. The microkeratome of claim 1, wherein said cutting head includes:
   upper and lower portions connected by a hinge that permits said cutting head to be opened for accessing said blade; and
   transmission means carried in the upper and lower portions and driven by said driving means for engaging and moving said cutting head over said guide ring at a controlled speed.

3. The microkeratome of claim 1, wherein said driving means includes means for inducing oscillatory motion in said blade that is transverse the cutting path.

4. The microkeratome of claim 1, wherein:
   said guide ring includes track means; and
   said cutting head includes transmission means driven by said driving means for engaging the track means and moving said cutting head over said guide ring at a controlled speed.

5. The microkeratome of claim 4, wherein the transmission means is positioned substantially within said cutting head, whereby the microkeratome has a narrow width that permits it to make an upper-to-lower cut through the ocular globe without interference with a patient's facial structure.

6. The microkeratome of claim 5, further comprising stop means for limiting the range through which said blade is carried through the cutting path so as to define a corneal hinge during a lamellar keratotomy, whereby the microkeratome is capable of defining a superior corneal hinge.

7. The microkeratome of claim 1, wherein said cornea compression device comprises an adjustable float head including:
   a pair of substantially parallel support arms; and
   a float having a triangular cross-section with three faces and being supported for rotation between the support arms about a journal that extends through the float, each of the three faces being spaced at different distances from the journal, whereby the thickness of the corneal resection is varied by rotation of the float until the desired face is in position to compress the cornea.

8. The microkeratome of claim 7, further comprising indicia on said float head for indicating the resection thickness provided by the selected face.

9. The microkeratome of claim 7, wherein at least one of the faces of the float is arcuate, whereby a corneal lenticular resection is performed by compressing the cornea with the one face.

10. The microkeratome of claim 7, wherein at least one of the faces of the float is oblique, whereby a corneal lenticular resection is performed by compressing the cornea with the one face.

11. The microkeratome of claim 10, further comprising means for automatically reversing said driving means when said stop means limits the range of said blade, whereby said microkeratome is returned to the position along said guide ring at which the surgery was initiated.

12. A microkeratome for performing a lamellar keratotomy of an ocular globe, comprising:
   a guide ring for placement on the ocular globe such that the globe's cornea protrudes therethrough, said guide ring including an upwardly extending pivot post;
   means for temporarily fixing said guide ring to the ocular globe;

a blade suitable for corneal resections;

a cutting head for carrying said blade over said guide ring through a cutting path;

a float head connected to said cutting head for at least partially compressing the cornea ahead of said blade so as to set the corneal resection to a predetermined shape and thickness; and means for driving said cutting head and said float head across said guide ring, including an output shaft that extends downwardly through said cutting head for engagement with the pivot post to constrain the output shaft against rotation relative to the pivot post, and means for applying a torque to the output shaft within said cutting head, whereby said cutting head and said float head are rotated about the output shaft by said driving means over said guide ring at a controlled speed and said blade cuts at least partially through the cornea to perform the lamellar keratotomy.

13. The microkeratome of claim 12, wherein:

said cutting head includes a hollow guide tube extending downwardly therefrom about the output shaft to guide the output shaft into engagement with the pivot post and to support the microkeratome above the guide ring on a plate at the base of the pivot post; and the pivot post and output shaft each include opposing complementary teeth means for axial engagement with one another.

14. The microkeratome of claim 13, wherein:

the guide tube includes a pin extending radially inwardly from its inner surface; and the pivot post includes a groove extending axially along the outer surface thereof, whereby the pin fits into the groove to ensure that the teeth of the output shaft are properly aligned for engagement with the teeth of the pivot post.

15. The microkeratome of claim 12, wherein:

said cutting head includes a hollow guide tube extending downwardly therefrom about the output shaft to guide the output shaft into engagement with the pivot post;

the output shaft is splined about its outer surface; and the pivot post is provided with a grooved opening complementing the splined output shaft.

16. The microkeratome of claim 12, further comprising stop means for limiting the range through which said blade is carried through the cutting path so as to define a corneal hinge during a lamellar keratotomy.

17. The microkeratome of claim 12, wherein said float head is adjustable so as to set the corneal resection to a desired shape and thickness.

18. A method of performing corneal resections for a lamellar keratotomy, comprising the steps of:

fixing a guide ring to an ocular globe about the globe's cornea so that the cornea extends through and above the guide ring;

applying a torque to the guide ring at a fixed point thereon to pivot a leading float head and a trailing cutting blade across the guide ring about the fixed point on the guide ring so that the float head sweeps in an arcuate path and compresses the cornea into a shape that complements the float head's lower surface and the blade sweeps in an arcuate path through a plane beneath the float head's lower surface so as to perform a corneal resection.

19. The method of claim 18, further comprising the step of adjustably stopping the cutting blade short of cutting completely through the cornea so as to define a corneal hinge.

20. The method of claim 19, wherein the resulting corneal hinge lies in the superior region of the cornea.

* * * * *